US011154566B2

(12) United States Patent
Choi et al.

(10) Patent No.: US 11,154,566 B2
(45) Date of Patent: Oct. 26, 2021

(54) COMPOSITION FOR PREVENTING HAIR LOSS OR PROMOTING HAIR GROWTH

(71) Applicant: CK BIOTECH, Seoul (KR)

(72) Inventors: Kang-Yell Choi, Seoul (KR); Jiyong Shim, Seoul (KR); Yeong Chan Ryu, Seoul (KR); Jiyeon Park, Seoul (KR)

(73) Assignee: CK BIOTECH, Seoul (KR)

(*) Notice: Subject to any disclaimer, the term of this patent is extended or adjusted under 35 U.S.C. 154(b) by 0 days.

(21) Appl. No.: 16/635,275

(22) PCT Filed: Jul. 31, 2018

(86) PCT No.: PCT/KR2018/008710
§ 371 (c)(1),
(2) Date: Jan. 30, 2020

(87) PCT Pub. No.: WO2019/027239
PCT Pub. Date: Feb. 7, 2019

(65) Prior Publication Data
US 2020/0179425 A1    Jun. 11, 2020

(30) Foreign Application Priority Data

Aug. 1, 2017 (KR) .................. 10-2017-0097539
Jul. 26, 2018 (KR) .................. 10-2018-0087096

(51) Int. Cl.
*A61P 17/14* (2006.01)
*A61K 9/107* (2006.01)
(Continued)

(52) U.S. Cl.
CPC .......... *A61K 31/7048* (2013.01); *A61K 9/107* (2013.01); *A61K 31/192* (2013.01);
(Continued)

(58) Field of Classification Search
None
See application file for complete search history.

(56) References Cited

U.S. PATENT DOCUMENTS

| 9,962,360 B2* | 5/2018 | Miller | A61P 17/02 |
| 2011/0130711 A1* | 6/2011 | Lederman | A61B 18/203 |
| | | | 604/22 |
| 2015/0165002 A1* | 6/2015 | Alabata | A61K 36/48 |
| | | | 424/94.67 |

FOREIGN PATENT DOCUMENTS

| CN | 101658518 | 3/2010 |
| CN | 104623026 | 5/2015 |

(Continued)

*Primary Examiner* — Melissa S Mercier
(74) *Attorney, Agent, or Firm* — Duane Morris LLP; Gregory M. Lefkowitz; Brandon A. Chan

(57) ABSTRACT

The present invention is about composition for preventing hair loss or promoting hair growth comprising indirubin derivatives; and one or more selected from the group consisting of Euodia daniellii extract, Persicaria hydropiper extract, Hovenia dulcis extract, methyl vanillate, hesperidin and quercitrin; as an active ingredient.

In addition, one or more selected from the group consisting of Euodia daniellii extract, Persicaria hydropiper extract, Hovenia dulcis extract, methyl vanillate, hesperidin and quercitrin of the present invention is a natural-derived composition with little toxicity to cells. Indirubin derivatives are stable compounds that have been found to have little toxicity to the human body, and therefore, when used in a mixture thereof, there are advantages in that they do not exhibit adverse effects on the human body, unlike conventional steroid drugs.

5 Claims, 12 Drawing Sheets

(51) Int. Cl.
*A61K 31/192* (2006.01)
*A61K 31/7048* (2006.01)
*A61K 31/353* (2006.01)
*A61K 31/4045* (2006.01)
*A61K 36/70* (2006.01)
*A61K 36/72* (2006.01)
*A61K 36/754* (2006.01)
*A61K 47/34* (2017.01)
*A61K 47/40* (2006.01)
*A61K 47/44* (2017.01)

(52) U.S. Cl.
CPC ........ *A61K 31/353* (2013.01); *A61K 31/4045* (2013.01); *A61K 36/70* (2013.01); *A61K 36/72* (2013.01); *A61K 36/754* (2013.01); *A61K 47/34* (2013.01); *A61K 47/40* (2013.01); *A61K 47/44* (2013.01); *A61P 17/14* (2018.01)

(56) References Cited

FOREIGN PATENT DOCUMENTS

| | | | |
|---|---|---|---|
| KR | 10-1975-0000105 | | 4/1975 |
| KR | 1019750000105 | * | 4/1975 |
| KR | 20100029672 | | 3/2010 |
| KR | 20170030175 | | 3/2017 |
| WO | 2015005603 | | 1/2015 |

* cited by examiner

COMPOSITION FOR PREVENTING HAIR LOSS OR PROMOTING HAIR GROWTH

CROSS-REFERENCE TO RELATED APPLICATIONS

This application is a § 371 national stage entry of International Application No. PCT/KR2018/008710, filed on Jul. 31, 2018, which claims priority to Korean Patent Application No. 10-2017-0097539, filed Aug. 1, 2017, and Korean Patent Application No. 10-2018-0087096, filed Jul. 26, 2018, the entire contents of which are incorporated herein by reference.

TECHNICAL FIELD

This invention relates to composition for preventing hair loss or promoting hair growth containing indirubin derivatives and plant extracts or small molecular compounds.

BACKGROUND TECHNOLOGY

There are about 100,000 to 150,000 hairs in the human body, which are formed in the hair follicles. Each hair is repeated in different cycles, with periods of anagen, catagen and telogen. The anagen phase is when hair grows, and the catagen phase is when the process of metabolism slows down, while the growth period ends and the shape of hair is maintained, which slows down the growth of hair growth. During the catagen phase, the cell division of the follicle stops and rapidly contracts. The telogen phase is when the follicle activity stops completely and the hair loss is prepared, and the hair at telogen phase is pushed out by the growing hair at the base and falls off its own, easily eliminated by physical action such as combing or washing of the hair. These cycles are repeated over three to six years periods.

In addition to hair loss caused by these natural phenomena, humans develop hair loss-related diseases due to aging, external environmental factors, and hormonal imbalances etc. Hair loss is a condition in which hair is not present in the area where it normally should exist. When hair loss occurs, the dermal papilla present in the hair bulb become smaller. As the dermal papillar become smaller, the hair becomes thinner and the hair cycle becomes shorter, and the newly grown hair grows thinner. As hair loss progresses, hair changes into fuzz and the hair cycle becomes shorter, so hair grows a little bit and falls right out.

Currently, the number of hair loss patients in Korea is estimated at 10 million, according to the Korean Hair Research Society. According to a 2011 tally by the Health Insurance Review and Assessment Service, nearly half of such hair loss patients were young people at their age of 20s or 30s. In other words, hair loss is no longer just a problem for older men, but for the majority of people.

Minoxidil and Propecia are commercialized as drugs to treat such hair loss. However, topically applicable Minoxidil can cause side effects such as edema, arrhythmia, and hair loss on unwanted areas in the long term, and the effect of Minoxidil is known to have the greatest effect between six months and a year after its use, and the effect gradually decreases. In cases of orally available Propecia, there have been reports of increased sexual dysfunction, depression and suicidal tendencies among patients who take them. Propecia is also not applicable to women during pregnancy or childbearing because it increases the chances of giving birth to deformed babies.

In addition, there is a problem of hair loss again if all of these drugs are discontinued. Although there is valproic acid as hair growth-promoting drug, it is known that taking it during pregnancy reduces a child's cognitive development ability. Although various types of hair growth-aiding techniques were generally used to promote blood circulation in the scalp and to provide nourishment for the hair, they are often toxic and have side effects with insufficient effects.

PREREQUISITE PATENT (Patent document) Korea Patent No. 10-1168051

CONTENTS OF INVENTION

The Tasks to Solve

This invention was developed to solve the above problems. The purpose of this invention is to provide hair loss prevention or hair growth promotion products that are effective as hair grower, hair growth promoters, and hair tonics containing indirubin derivatives and plant extracts or small molecular compounds as ingredients of the plant extract with no adverse effects on the human body.

In addition, the above Indirubin derivatives and plant extracts or small molecular compounds described in this invention are provided with cosmetic products or health-functioning food products that are effective in promoting hair growth and preventing hair loss.

The Method to Solve

To achieve the above objective, this invention provides compositions for preventing hair loss or promoting hair growth that comprises indirubin derivatives; and one or more selected from the group consisting of Euodia daniellii extract, Persicaria hydropiper extract, Hovenia dulcis extract, methyl vanillate, hesperidin and quercitrin; as an active ingredient.

The above extracts could be extracted by water, DMSO, alcohol of carbon number 1 to 4, or their mixture.

The above extract may be obtained from the stem, leaf, or their pulverizer, and its mixture into solvents selected from a group of DMSO, n-hexane, ethanol, ethylacetate, butanol and their mixed solvent.

The above indirubin derivatives are one or more of its choice from a group of 5-Methoxylindirubin-3'-oxime, Indirubin-3'-oxime, 6-Bromindirubin-3'-oxime, 5,6-dichloroindirubin, 5,6-dichloroindirubin-3'-oxime, 5,6-dichloroindirubin-3'-methoxime, 5,6-dichloroindirubin-3'-propyloxime, 6-Chloro-5-nitroindirubin, 6-Chloro-5-nitroindirubin-3'-oxime, 6-chloroindirubin-3'-methoxime, 5-Chloroindirubin-3'-methoxime, 5-Bromoindirubin-3'-oxime, 5-Bromoindirubin-3'-methoxime, 5-Bromoindirubin-3'-ethyloxime, 5,6-dichloroindirubin-3'-propyloxime, 6-chloroindirubin-3'-benzyloxime etc.

The Indirubin derivative above may be one or more of the following selected items, as shown in formula 1 or formula 4.

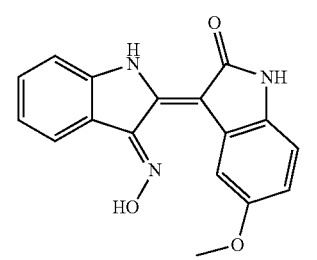

[Chemical formula 1]

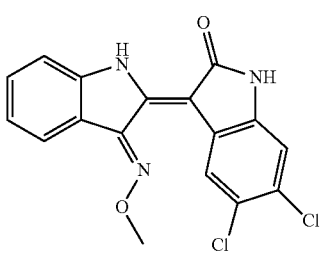

[Chemical formula 2]

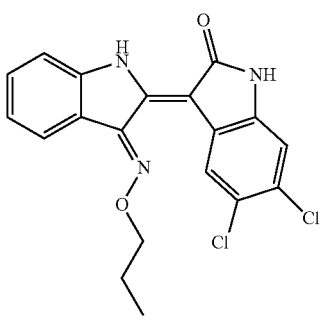

[Chemical formula 3]

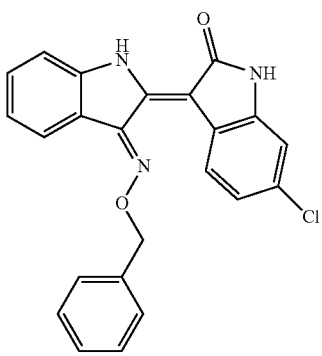

[Chemical formula 4]

Based on the dry weight of the above extract, the above Indirubin derivatives may contain 5 to 15 masses.

The above extract may be included as a dry weight of 5 percent within 0.001 or as a liquid weight of 0.001 to 50 percent.

The above composition may be an emulsion form that contains more oil, surfactant and polyethylene glycol.

The mixed weight ratio of the above oil, surfactant and polyethylene glycol may be 0.3-30:1:2-2.5.

The surfactants are selected from any polyoxyethylene sorbitane monorraurate (Tween 20), polyoxyethylene sorbitan monopalmitate (Tween 40), polyoxyethylene sorbitan monostearate (Tween 60), polyoxyethylene sorbitan oleate, (Tween 80).

The above oil may be any one or more selected from the group consisting of polyethoxylated castor oil (Kolliphor® EL), sunflower oil and olive oil.

The composition may include cyclodextrin for higher solubilization. 100 to 1000 parts by weight of cyclodextrin may be based on 100 parts by weight of the active ingredient present in the composition.

The emulsion formulations may be stable formulations that will not change the Wnt activity and solubility in distilled water under conditions of 25 to 4° C. as measured at 3 months.

The present invention to achieve the above other object, indirubin derivatives; and one or more selected from the group consisting of Euodia daniellii extract, persicaria hydropiper extract, hovenia dulcis extract, methyl vanillate, hesperidin and quercitrin; for promoting growth of dermal papilla cells isolated from the skin of a mammal comprising as an active ingredient to provide a composition.

The composition may be to promote growth length of hair follicles or proliferation of dermal papilla cells in vitro.

The composition may be an emulsion formulation further comprising an oil, a surfactant and polyethylene glycol.

The mixed weight ratio of the oil, the surfactant, and the polyethylene glycol may be 0.3-30:1:2-2.5.

The composition may include cyclodextrin for higher solubilization. 100 to 1000 parts by weight of cyclodextrin may be included based on 100 parts by weight of the active ingredient present in the composition.

In order to achieve the above or another object, the present invention provides an indirubin derivative; provides a cosmetic composition for preventing hair loss or promoting hair growth comprising indirubin derivatives; and one or more selected from the group consisting of Euodia daniellii extract, Persicaria hydropiper extract, Hovenia dulcis extract, methyl vanillate, hesperidin and quercitrin; as an active ingredient.

The cosmetic composition may be any one hair formulation selected from the group consisting of shampoo, spray, rinse, hair, gel, hair tonic, hair lotion, soap or hair pack.

The composition may be an emulsion formulation further comprising an oil, a surfactant and polyethylene glycol.

The mixed weight ratio of the oil, surfactant, and polyethylene glycol is 0.3-30:1:2-2.5.

The composition may include cyclodextrin for higher solubilization. 100 to 1000 parts by weight of cyclodextrin may be included based on 100 parts by weight of the active ingredient present in the composition.

The present invention to achieve another object, the present invention provides a health functional food for hair growth promotion comprising indirubin derivatives; and one or more selected from the group consisting of Euodia daniellii extract, Persicaria hydropiper extract, Hovenia dulcis extract, methyl vanillate, hesperidin and quercitrin; as an active.

Effect of Invention

The composition according to the present invention can be usefully used as a pharmaceutical composition or cosmetic composition that can prevent hair loss or promote hair growth, and can be utilized in hair loss prevention or hair growth promoting functional cosmetics exerted from the hair loss preventing function, including a hair growth promoter.

In addition, any one or more selected from the group consisting of Euodia daniellii extract, Persicaria hydropiper extract, Hovenia dulcis extract, methyl vanillate, hesperidin and quercitrin of the present invention is a naturally derived composition without any significant toxicity to cells. Indirubin derivatives are stable compounds that have been found to have little toxicity to the human body, and therefore, when used in a mixture of these, there are advantages in that they do not exhibit adverse effects on the human body, unlike conventional steroid drugs.

The present invention is a composition in which any one or more selected from the group consisting of indirubin derivatives and Euodia daniellii extract, Persicaria hydropiper extract, Hovenia dulcis extract, methyl vanillate, hesperidin and quercitrin are mixed in a certain ratio, and has a stronger effect on the hair growth promotion and hair loss prevention compared to the single composition.

DETAILED DESCRIPTION FOR CARRYING OUT THE INVENTION

Figure 1A:
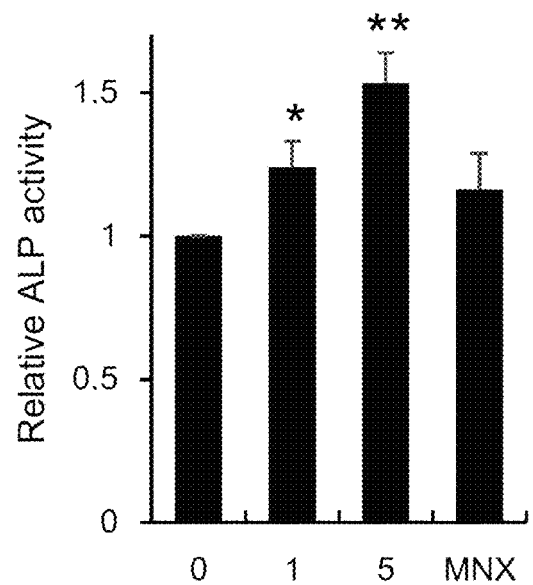
FIG. 1a is a graph showing the quantitative measurement of ALP (alkaline phosphatase) activity following the treatment of the complex prepared from embodiment 2 in human dermal papilla cells.

Hereinafter, various aspects and various examples of the present invention will be described in more detail.

One aspect of the present invention is a composition for preventing hair loss or promoting hair growth comprising indirubin derivatives; and one or more selected from the group consisting of Euodia daniellii extract, Persicaria hydropiper extract, Hovenia dulcis extract, methyl vanillate, hesperidin and quercitrin; as an active.

The present invention is a complex of indirubin derivatives and one or more selected from the group consisting of Euodia daniellii extract, Persicaria hydropiper extract, Hovenia dulcis extract, methyl vanillate, hesperidin and quercitrin in a certain ratio, to prevent hair loss and promote hair growth. They can be applied to various fields such as pharmacy, food, cosmetics because they show an excellent effect on preventing hair loss and promoting hair growth.

The above indirubin derivatives are one or more of its choice from a group of 5-Methoxylindirubin-3'-oxime, Indirubin-3'-oxime, 6-Bromindirubin-3'-oxime, 5,6-dichloroindirubin, 5,6-dichloroindirubin-3'-oxime, 5,6-dichloroindirubin-3'-methoxime, 5,6-dichloroindirubin-3'-propyloxime, 6-Chloro-5-nitroindirubin, 6-Chloro-5-nitroindirubin-3'-oxime, 6-chloroindirubin-3'-methoxime, 5-Chloroindirubin-3'-methoxime, 5-Bromoindirubin-3'-oxime, 5-Bromoindirubin-3'-methoxime, 5-Bromoindirubin-3'-ethyloxime, 5,6-dichloroindirubin-3'-propyloxime, 6-chloroindirubin-3'-benzyloxime etc.

Preferably, the indirubin derivative is hardly toxic to cells even after long-term treatment, and any of those selected from the following formulas 1 to 4 having a significant increase in effect when treated with extracts. It may be one or more, and most preferably may be an indirubin derivative represented by the following formula 2. Because the treatment of indirubin derivatives of the formula 2 and Euodia daniellii extract showed faster growth in the dermal papilla cells 2.5 times or more compared with the case where the indirubin derivatives 1 to 4 were treated alone. In other words, the indirubin derivatives used together with the natural product extracts (Euodia daniellii extracts, Persicaria hydropiper extracts, Hovenia dulcis extracts) may be any one or more selected from those represented by the following Chemical Formulas 1 to 4, but most preferably 5, 6-dichloroindirubin-3'-methoxime (Formula 2).

complex was confirmed the proliferative effect of the dermal papilla cells by the extract alone or a mixture of the extract and any one or more indirubin derivatives selected from those represented by the Formula (1) to (4). The result was good in ALP activity. In particular, when the Euodia daniellii extracts and the indirubin derivative (A3334) is mixed, it was confirmed that the results of 1.5 times higher at a concentration 10 times smaller than when treated with Euodia daniellii extracts alone.

In addition, it was confirmed that the hair fiber length of the nose hair follicles was increased by treating the cultured hair follicles isolated from the mouse with a complex mixed with the extract and the indirubin derivatives of the formulas 1 to 2.

The composite mixture of the extract and the indirubin derivative of Formula 1 or Formula 2 showed a four-fold increase in length even though the concentration was 100-1000 times less than the conventional hair loss treatment. The indirubin derivative of Formula 1 (Example The composite comprising 1) was found to have an unexpectedly significant increase of 2.5 times or more, despite being 10 times lower in concentration than the Embodiments 2, 3, and 4 composites.

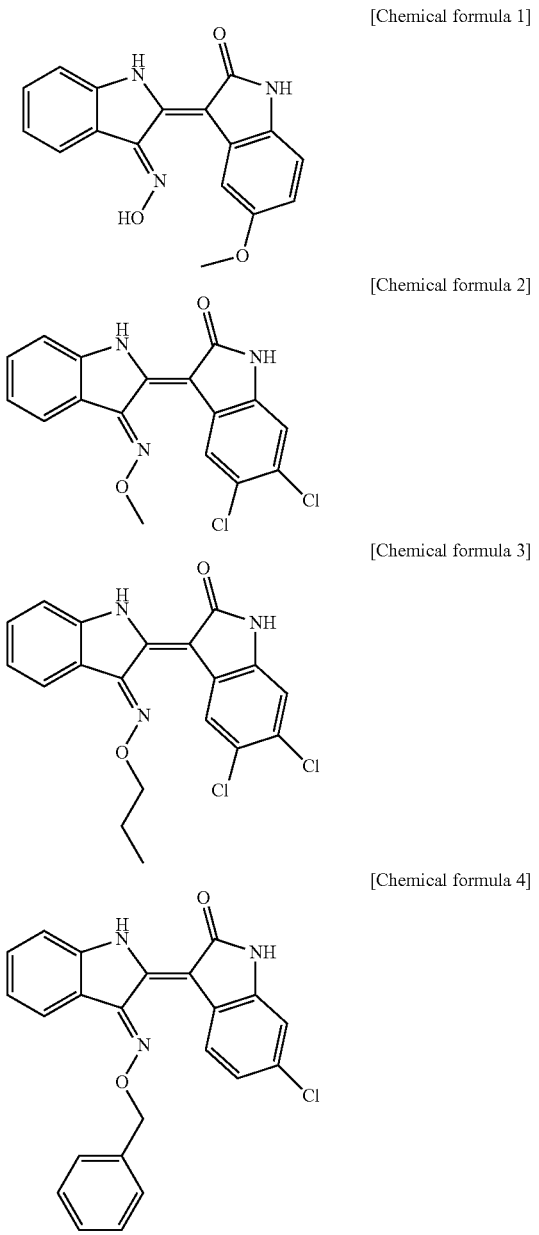

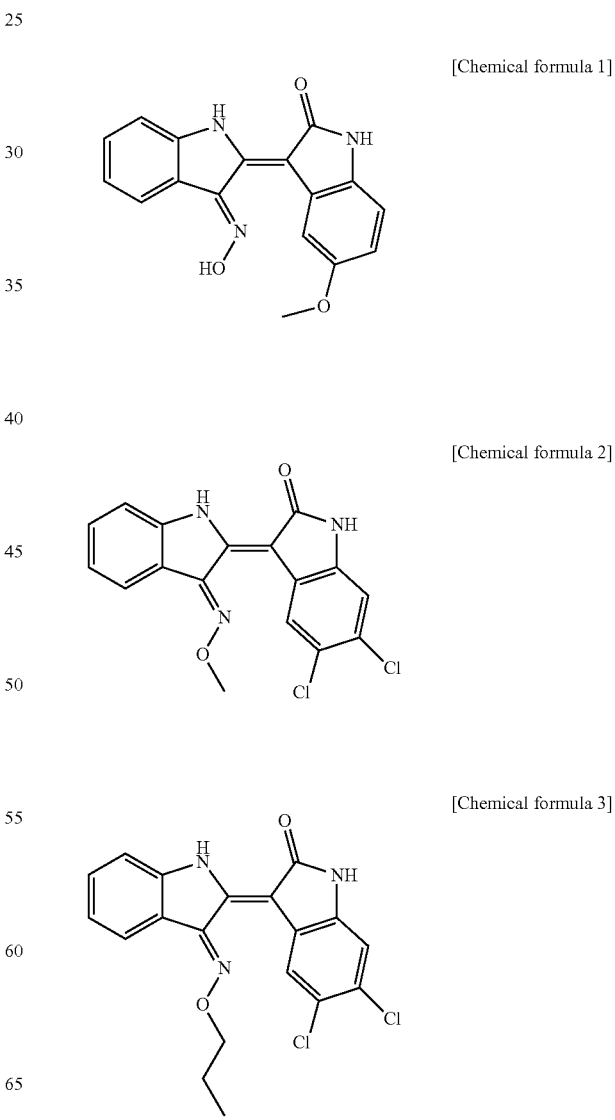

Any one or more indirubin derivatives selected from the ones represented by the above formulas (1) and (4); and one or more selected from the group consisting of Euodia daniellii extract, persicaria hydropiper extract, hovenia dulcis extract, methyl vanillate, hesperidin and quercitrin. As shown in the following Embodiments and Figures, the -continued

[Chemical formula 4]

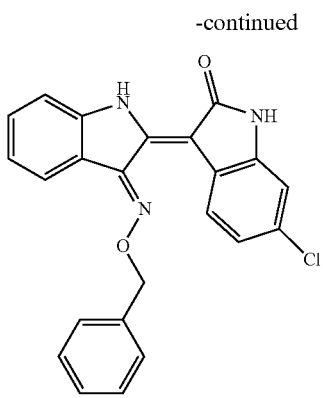

Therefore, a complex of one or more indirubin derivatives selected from the ones represented by the above formulas 1 to 4; and Euodia daniellii extract, Persicaria hydropiper extract, Hovenia dulcis extract, methyl vanillate, hesperidin and quercitrin, which is a mixture of any one or more, may be used as a pharmaceutical composition and a cosmetic composition for maintaining anagen phase and preventing hair follicles from entering into telogen phase, thereby preventing hair loss and promoting hair growth.

In the use of indirubin derivatives, Euodia daniellii extract, Persicaria hydropiper extract, Hovenia dulcis extract, methyl vanillate, hesperidin and quercitrin alone, there was a limit to increasing the dose to enhance the effect. In particular, even if each of the components have a hair growth-promoting effect, mixing them does not necessarily have the effect of combining the respective components, but rather the effect of hair growth that can be reduced or obtained by mixing different components. Most of them were insignificant. In this situation, through a number of repeated experiments, when an indirubin derivative is mixed with any one of natural extracts such as Euodia daniellii extract, Persicaria hydropiper extract, hovenia dulcis extract, or any one of natural extracts such as methyl vanillate, hesperidin and quercitrin, as a result of confirming substantial and significant hair growth than the effect that can be obtained by simply increasing the respective doses, it can be seen that an excellent effect can be obtained even with the addition of a low dose without any reduction or obstruction in terms of efficacy.

The above methyl vanillate, hesperidin and quercitrin is a component contained in the extract of Euodia daniellii extracts, Hovenia dulcis extracts, Citrus extracts, Polygonum aviculare extracts, Persicaria hydropiper extracts, Houttuynia cordata extracts. The above methyl vanillate is mainly present in the Hovenia dulcis extracts, the above hesperidin is mainly present in the Euodia daniellii extracts and Citrus extracts, the above quercitrin is mainly present in the Persicaria hydropiper extracts, Polygonum aviculare extracts, Houttuynia cordata extracts.

It is preferable to include indirubin derivatives (Formula 2); and one or more selected from the group consisting of Euodia daniellii extract, persicaria hydropiper extract, hovenia dulcis extract, methyl vanillate, hesperidin and quercitrin as an active ingredient. Because combinatorial treatment with hesperidin or quercitrin and indirubin derivatives (Formula 2) can achieve more than twice hair growth promoting effect at 5 times lower contents than when used indirubin derivatives alone or them with methyl vanillate.

The composition according to the present invention has a hair growth promoting effect as well as maximizing the proliferation of cells in hair follicles and dermal papilla cells play an important role in hair diseases.

In particular, dermal papilla cells are tissues derived from endodonitis at the base of hair follicles which are involved in hair development, growth, and cycle regulation. The dermal papilla cells (mesenchymal cells) secrete substances that induces the production of hair and subsequently stimulates hair growth in the developmental phase, and the degenerative phase begins with the change of the dermal papilla cells. During the resting phase, hair stem cells divide by the signals of the dermal papilla cells and a growth phase begins to form new hair follicles.

Alopecia is mainly affected by proliferation and cell number of the dermal papilla, among several factors. Since the composition according to the present invention promotes the growth of dermal papilla cells, it can be seen that it has a useful effect in preventing hair loss or promoting hair growth of the dermal papilla cells.

The indirubin derivative used in the present invention may be provided not only as a free substance but also as a pharmaceutically acceptable salt, pharmaceutically acceptable solvate, pharmaceutically acceptable polymorph or pharmaceutically acceptable prodrug thereof. The salt of the indirubin derivative is not particularly limited as long as it is a form that can be blended in medicine or cosmetics. Inorganic salts or organic salts, and may be acid salts or alkaline salts. Especially in the case of salts with cations, alkaline earth metal salts such as sodium salts and potassium salts, calcium salts, magnesium salts and barium salts; Basic amino acid salts such as arginine and lysine; Ammonium salts such as ammonium salt and tricyclohexyl ammonium salt; And various alkanol amine salts such as monoethanolamine salt, diethanolamine salt, triethanolamine salt, monoisopropanolamine salt, diisopropanolamine salt and triisopropanolamine. Preferably the salt is an alkali metal salt, more preferably may be tetrasodium salt.

The composition according to the present invention exhibits an excellent effect of preventing hair loss or promoting hair growth, and may be usefully used to prevent hair loss and promote hair growth when hair loss due to hair loss or hair growth is slow.

Mixed weight ratios one or more indirubin derivatives selected from those represented by Formula 1 to Formula 4; and one or more selected from the group consisting of Euodia daniellii extract, Persicaria hydropiper extract, Hovenia dulcis extract, methyl vanillate, hesperidin and quercitrin is not particularly limited thereto. However, when one or more indirubin derivatives selected from those represented by Chemical Formulas 1 to 4 and natural product extracts (Euodia daniellii extract, persicaria hydropiper extract, hovenia dulcis extract) are mixed, it is preferable that the indirubin derivative is mixed in an amount of 5 to 15 parts by weight based on the dry weight part 10 of the extract, more preferably 9 to 11 parts by weight. Outside the above range, it is not preferable because the hair loss prevention and hair promoting effect is lowered.

Any one or more small molecules selected from the group consisting of methyl vanillate, hesperidin and quercitrin, if the composition is a mixture of indirubin derivatives represented by the Formulas 1 to 4 and at least one selected from methyl vanillate, hesperidin and quercitrin. The mixing weight ratio of the compound and indirubin derivative is not particularly limited thereto. However, it is preferable that the low molecular weight compound and the indirubin derivative are mixed with the indirubin derivative in a 1 to 20 molar ratio based on 1 mole of the low molecular weight compound. If it is out of the above range, the increase of hair loss prevention and hair promoting effect may be insignificant.

Since the composition of the present invention promotes hair growth, it is not involved in promoting hair growth through regulating testosterone and/or blood circulation. Therefore, it may be effective in improving hair loss that could not be solved by inhibiting male hormones or promoting blood circulation.

The above composition is not particularly limited as long as the concentration is included in the extract is a general range in the art, the extract may be included in 0.001 to 5% by weight or 0.001 to 50% by weight of the dry weight relative to the total weight of the composition. If less than 0.01% by weight, it may not exhibit a sufficient hair loss prevention or hair growth promoting effect. If it exceeds 5% by weight (dry weight) or 50% by weight (liquid weight), excessive amounts of the solvent included in the extract may cause skin irritation.

The above extract is a pulverized powders of stem and leaves, and mixtures thereof are extracted using water, DMSO, alcohol having 1 to 4 carbon atoms and mixed solvents thereof.

The extract can be obtained by fractionation with a solvent selected from the group consisting of a pulverized product, and mixtures thereof in the stems, leaves of Euodia daniellii, Persicaria hydropiper, Hovenia dulcis in DMSO, n-hexane, ethanol, ethyl acetate, butanol and mixed solvents thereof have.

On the other hand, the term 'comprising as an active ingredient' used herein means containing an amount sufficient to treat hair loss prevention or hair growth promotion of the present invention.

The composition for hair loss prevention or hair growth promotion of this invention may be applied in local administration by e.g. oral administration or injection or non-varying administration or application of the product in general in the party industry. The appropriate dosage of the compounds in this invention may vary depending on the patient's condition and weight, degree of disease, drug-type administration pathways and duration, and may be appropriately selected by the party. However, most preferred may be topical administration by parenteral administration or application.

When the composition of the present invention is an oral or injectable mode of administration, the composition according to the present invention may further comprise suitable carriers, excipients and diluents commonly used in the manufacture of a medicament. Each can be used in the form of powders, granules, tablets, capsules, suspensions, emulsions, syrups, aerosols and the like, oral formulations, external preparations, suppositories, and sterile injectable solutions according to conventional methods.

Carriers, excipients and diluents that may be included in the compositions of the present invention include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil.

When formulated, diluents or excipients such as fillers, extenders, binders, wetting agents, disintegrating agents and surfactants are usually used. Solid form preparations for oral administration include tablets, pills, powders, granules, capsules and the like, and such solid form preparations include at least one excipient such as starch, calcium carbonate, sucrose, lactose, gelatin, etc. are mixed and prepared. In addition to simple excipients, lubricants such as magnesium stearate and talc are also used. Oral liquid preparations include suspensions, solvents, emulsions, and syrups, and may include various excipients, such as wetting agents, sweeteners, fragrances, and preservatives, in addition to commonly used simple diluents such as water and liquid paraffin. Preparations for parenteral administration include sterile aqueous solutions, non-aqueous solvents, suspensions, emulsions, lyophilized preparations, suppositories. As the non-aqueous solvent and suspending agent, propylene glycol, polyethylene glycol, vegetable oil such as olive oil, injectable ester such as ethyl oleate, and the like can be used. As the base of the suppository, witepsol, macrogol, tween 61, cacao butter, laurin butter, glycerol gelatin and the like can be used.

The desired dose of the composition of this invention depends on the condition and weight of the patient, the degree of disease, the form of the drug, the route of administration, and the duration, but may be appropriately selected by the party. However, for the desired effect, it is recommended that the composition of this invention be administered at 0.0001 to 10 g/kg per day and at 0.001 to 8 mg/kg as preferably. Administration may be administered once a day or may be divided several times. The dosage does not limit the scope of the invention in any aspect. Preferably, it may be administered in the range of 0.1 mg to 10 mg, 0.25 mg to 5 mg, 0.5 mg to 2 mg per day. For example, it can be administered as 0.125 mg, 0.25 mg, 0.5 mg, 0.75 mg, 1 mg, 1.5 mg, 2 mg per day.

Furthermore, the compositions of the present invention may be parenteral or topical, with topical administration being most preferred by direct application to the skin.

If the above composition is formulated to be locally applied in the form of liquid, cream, lotion, gel or aerosol, it may include suitable ordinary additives, e.g. preservatives, solvents that assist in the penetration of medicine, softening agents in the case of ointment and cream. The above local preparation may also contain commercially available ordinary solids, for example cream and oleil alcohol for ointment base and lotion. The carrier above may comprise about 1 to about 98% of the formulation, and more generally up to about 80% of the formulation.

A product for hair loss prevention or hair growth promotion under this invention may be a formulation that can be administered by methods such as applying or dispensing directly to the skin, for example, cream, roo-shion, ointment, aerosol, gel, or pack. The method for the composition or preparation of the composition of each form is well known in the Party business community. In manufacturing these products, the Party may select and use the various compounds used to manufacture the ordinary external agents.

Such components include, in the case of ointments, creams, gels, lotions, white petrolatum, yellow petrolatum, lanolin, bleached beeswax, cetanol, stearyl alcohol, stearic acid, hardened oil, gelled hydrocarbons, polyethylene glycol, There are bases such as liquid paraffin and squalane, and oleic acid, isopropyl myristate, glycerin triisooctanoate, crotamiton, diethyl sebacate, diisopropyl adipicate, hexyl laurate, fatty acid, fatty acid ester, aliphatic Solvents and dissolution aids such as alcohols and vegetable oils, and antiseptics such as tocopherol derivatives, L-ascorbic acid, dibutylhydroxytoluene, butylhydroxyanisole, and preservatives such as parahydroxybenzoic acid esters, glycerin, and propylene. Moisturizing agents such as glycol and sodium hyaluronate, polyoxyethylene derivatives, glycerin fatty acid esters, sucrose fatty acid esters, sorbides There is a thickener such as fatty acid esters, propylene glycol fatty acid ester, lecithin, etc. of the surface active agent, carboxyvinyl polymer, xanthan gum, carboxymethyl cellulose, carboxymethyl cellulose sodium salt, hydroxypropyl cellulose, hydroxypropyl methyl cellulose.

In the case of aerosols, in addition to the above components used in the preparation of ointments, creams, gels, suspensions, emulsions, solutions, lotions and the like, various stabilizers, buffers, copulating agents, suspending agents, emulsifiers, fragrances, preservatives, dissolution aids, and other suitable additives may be blended.

The formulation of the composition for preventing hair loss or promoting hair growth according to the present invention may preferably be an emulsion formulation further comprising an oil, a surfactant, and polyethylene glycol.

In the emulsion formulation, the mixed weight ratio of the oil, surfactant and polyethylene glycol may be 0.3-30:1:2-2.5, more preferably 10-20:1:2-2.5. The composition of the above emulsion formulation may be determined by a similar three-phase diagram drawn up according to the usual method to determine the composition of the emulsion system. Specifically, the oil phase (polyethoxylated castor oil (Kolliphor® EL)) and the surfactant (eg a mixture of tween 80 and polyethylene glycol) are thoroughly mixed in different weight ratios in a specific ratio range. The pseudo-three phase diagram can then be created by adding water to each proportion of the oil and surfactant mixture and marking the points corresponding to the emulsion forming region. By determining the emulsion region from a similar three-phase diagram prepared, the key to the above validation (a mixture of indirubin derivatives and one or more selected from a group of Euodia daniellii extract, Persicaria hydropiper extract, Hovenia dulcis extract, methyl vanillate, hesperidin and quercitrin) can be determined by melting emulsion.

If these compounds are emulsion-types, it is desirable that the above effective compounds (complexes containing indirubin derivatives and one or more selected from a group of Euodia daniellii extract, Persicaria hydropiper extract, Hovenia dulcis extract, methyl vanillate, hesperidin and quercitrin) are included in the total volume of the compounds.

The above surfactant acts as an auxiliary de-ionizing agent for the twin series of non-ionic surfactants, used in pharmaceuticals as an emulsifier or wetting agent for oral or non-vigid agents, and as an additive in cosmetics or food. It is also used as a substance for suppressing p-glycoproteins to increase bioavailability of drugs. Tween-based surfactants include polyoxyethylene sorbitan monolaurate (Tween 20), polyoxyethylene sorbitan monopalmitate (Tween 40), polyoxyethylene sorbitan monostearate (Tween 60) and polyoxyethylene sorbitan oleate (Tween 80), including but not limited to any one or more selected from the group consisting of. The above Twin series of surfactants is a stable substance licensed by the U.S. Food and Drug Administration for use in intravenous injections of the human body.

In addition, the above polyethylene glycol is a two-sided polymer with hydrophobic and hydrophobic properties, which is a liquid at low molecular weight, but becomes solid as the molecular weight increases. The polyethylene glycol above may be used either of the selected polyethylene glycols from a group of PEG 150, 300, 400, 1000, 6000, 8000, 10000, 20000, 30000 and 40000 which means polyethylene glycol with a molecular weight exceeding 10,000 is also referred to as polyethylene oxide (PEO). Among these, PEG400 exists in the form of a liquid, and is frequently used for solubilizing various poorly soluble drugs, and especially for the oral and parenteral (intravenous injection, subcutaneous injection, intramuscular injection, etc.) of the human body as a stable substance that is authorized in the US Food and Drug Administration (FDA).

The surfactant used in the embodiment of the present invention is polyoxyethylene sorbitan oleate (Tween 80), and polyethylene glycol is PEG 400, which has amphiphilic properties and is dispersible in water. At least one selected from the group consisting of poorly soluble active ingredients (indirubin derivatives represented by any one of the Formulas 1 to 4 and Euodia daniellii extract, Persicaria hydropiper extract, Hovenia dulcis extract, methyl vanillate, hesperidin and quercitrin emulsion formulation), which is optimized for this mixed compound).

The above oil may be one or more selected from a group of polytoxylated pyjamasyl, sunflower oil and olive oil.

The above composition may contain cyclodextrin for higher availability. Cyclodextrin may include 100 to 1000 weights based on the effective 100 weights present in the above composition.

When measured in the third month, the above emulsion formulation is a stable form that does not show changes in the activity and solubility of Wnt in distilled water under the conditions of temperature of 25° C. to 4° C. It is confirmed that the activity of the effective ingredient can be maintained for a long period of time, and absorption into the body can be effectively altered.

In addition, the methods of manufacture of emulsion compounds for hair loss prevention or hair growth promotion, including any one or more of the above-mentioned indirubin derivatives and Euodia daniellii extract, Persicaria hydropiper extract, Hovenia dulcis extract, methyl vanillate, hesperidin and quercitrin, are as follows.

1) The process of making the first solution by mixing oil, surfactant and polyethylene glycol;

2) The stage in which a second solution containing the validity of the above Indirubin derivatives and one or more selected from the group consisting of Euodia daniellii extract, Persicaria hydropiper extract, Hovenia dulcis extract, methyl vanillate, hesperidin and quercitrin is manufactured;

3) The phase of the manufacture of emulsion compounds by mixing the second solution with the above 1st solution is included.

The above 2nd solution may contain more cyclodextrin.

The above polyethylene glycol is a two-sided polymer that has hydrophilic and hydrophobic properties, which is a liquid when low-molecule, but becomes solid when the molecular weight increases. The polyethylene glycol may be any one selected from the group consisting of PEG 150, 300, 400, 1000, 6000, 8000, 10000, 20000, 30000 and 40000. In this case, the PEG300 means polyethylene glycol having a molecular weight of 300, and polyethylene glycol having a molecular weight of more than 10,000 may be referred to as polyethylene oxide (PEO). Among them, PEG400 exists in the form of a liquid, and is frequently used for solubilizing various poorly soluble drugs, and especially used in the oral and parenteral (intravenous injection, subcutaneous injection, intramuscular injection, etc.) of the human body as a stable substance that is authorized by the US Food and Drug Administration (FDA).

The above surfactant acts as an auxiliary de-ionizing agent for the twin series of non-ionic surfactants, used in pharmaceuticals as an emulsifier or wetting agent for oral or non-vigid agents, and as an additive in cosmetics or food. It is also used as a substance for suppressing p-glycoproteins to increase bioavailability of drugs. Tween-based surfactants include polyoxyethylene sorbitan monolaurate (Tween 20), polyoxyethylene sorbitan monopalmitate (Tween 40), polyoxyethylene sorbitan monostearate (Tween 60) and polyoxyethylene sorbitan oleate (Tween 80), including but not limited to any one or more selected from the group consisting of. The above Twin series of surfactants is a stable substance licensed by the U.S. Food and Drug Administration for use in intravenous injections of the human body.

The mixed weight ratio of the above oil, surfactant and polyethylene glycol may be 0.3-30:1:1:2-2.5 and, more desirable, 10-20:1:2-2.5. If the above composition is emulsion-type, it is desirable that the above effective ingredients (the compound of indirubin derivatives and extracts) are included in the total weight of the composition by 1 to 20 percent.

The emulsion of this invention was completely dissolved, forming an emulsion form (F8) in the solution, after taking a microscope picture with water added to the emulsion composition of this invention. The stability of the emulsion of this invention was observed, and the average diameter was measured between 20 and 1500 nm and the desired diameter was 30 to 50 nm to form a liquid of nanoscale, indicating a narrow range of size distributions.

In addition, the emulsion of this invention was confirmed to maintain stability for a long period of time, with no changes in solubility and active changes in the effective ingredients for three months at room temperature. Furthermore, the absorption can be improved effectively if the emulsion formulation of this invention is applied to oral administration or local areas.

In another aspect, the present invention is indirubin derivatives and one or more selected from the group consisting of Euodia daniellii extract, Persicaria hydropiper extract, Hovenia dulcis extract, methyl vanillate, hesperidin and quercitrin an active ingredient, from the skin of mammals. Provided is a composition for promoting growth of isolated dermal papilla cells or hair follicle cells.

The composition comprising an indirubin derivatives and one or more selected from the group consisting of Euodia daniellii extract, Persicaria hydropiper extract, Hovenia dulcis extract, methyl vanillate, hesperidin and quercitrin an active ingredient, promotes dermal papilla cells or hair follicle cells in vitro. It can be used as the composition that can promote the proliferation of, in particular can be utilized as a medium composition for culturing the dermal papilla cells and hair follicle cells.

The mammal may be any one selected from the group consisting of human, cow, goat and sheep.

The present inventors provide a composition which can efficiently and rapidly mass-produce dermal papilla cells or hair follicle cells ex vivo in connection with hair loss or hair growth promotion, and the composition only efficiently grows dermal papilla cells or hair follicle cells. In addition, it was found that a large amount of dermal papilla cells and hair follicle cells grown without toxicity can be produced in high yield.

Formulation of the composition for promoting growth of dermal papilla cells or hair follicle cells according to the present invention may preferably be an emulsion formulation further comprising an oil, a surfactant and polyethylene glycol.

In the emulsion formulation, the mixed weight ratio of the oil, surfactant and polyethylene glycol may be 0.3-30:1:2-2.5, more preferably 10-20:1:2-2.5. The composition of the above emulsion formulation may be determined by a similar three-phase diagram drawn up according to the usual method to determine the composition of the emulsion system. Specifically, the oil phase (polyethoxylated castor oil (Kolliphor® EL)) and the surfactant (e.g., a mixture of tween 80 and polyethylene glycol) are thoroughly mixed in different weight ratios in a specific ratio range.

Similar three-phase diagrams can be prepared by adding water to each proportion of the oil and surfactant mixture and marking the points corresponding to the emulsion-forming region. In the similar three-phase diagram, the emulsion region is determined, and a specific composition is selected among the compositions included in the region, and the active ingredient (indirubin derivative and Euodia daniellii extract, persicaria hydropiper extract, hovenia dulcis extract, methyl vanillate, hesperidin and quercitrin) It can be determined by the composition of the emulsion formulation to dissolve any one or more selected from the group consisting of.

If the composition is an emulsion formulation, the active ingredient (indirubin derivatives and Euodia daniellii extract, Persicaria hydropiper extract, Hovenia dulcis extract, methyl vanillate, hesperidin and quercitrin is mixed with any one or more selected from the group consisting of Compound) is preferably included 1 to 20% by weight based on the total weight of the composition.

The surfactant serves as a co-solvent as a twin-based nonionic surfactant, and is used as an emulsifier or humectant in oral or parenteral preparations in pharmaceuticals, and as an additive in cosmetics or foods. It is also used as a substance for inhibiting p-glycoprotein to increase the bioavailability of the drug. Tween-based surfactants include polyoxyethylene sorbitan monolaurate (Tween 20), polyoxyethylene sorbitan monopalmitate (Tween 40), polyoxyethylene sorbitan monostearate (Tween 60) and polyoxyethylene sorbitan oleate (Tween 80), including but not limited to any one or more selected from the group consisting of. The above Twin series of surfactants is a stable substance licensed by the U.S. Food and Drug Administration for use in intravenous injections of the human body.

In addition, the above polyethylene glycol is a two-sided polymer with hydrophobic and hydrophobic properties, which is a liquid at low molecular weight, but becomes solid as the molecular weight increases. The polyethylene glycol may be any one selected from the group consisting of PEG 150, 300, 400, 1000, 6000, 8000, 10000, 20000, 30000 and 40000. In this case, the PEG300 refers to polyethylene glycol having a molecular weight of 300, and polyethylene glycol having a molecular weight of more than 10,000 may be referred to as polyethylene oxide (PEO). Among them, PEG400 exists in the form of a liquid, and is frequently used for solubilization of various poorly soluble drugs, and especially in the US Food and Drug Administration (FDA) for oral and parenteral (intravenous injection, subcutaneous injection, muscle injection, etc.) of the human body. It is a stable substance licensed for use.

The surfactant used in the embodiment of the present invention is polyoxyethylene sorbitan oleate (Tween 80), and polyethylene glycol is PEG 400, which has amphiphilic properties and is dispersible in water. Emulsion formulations, optimized for poorly soluble active ingredients (complex of any one selected from the group consisting of indirubin derivatives and Euodia daniellii extract, Persicaria hydropiper extract, Hovenia dulcis extract, methyl vanillate, hesperidin and quercitrin) can be provided.

The above oil may be any one or more selected from the group consisting of polyethoxylated castor oil (Kolliphor® EL), sunflower oil and olive oil.

The above composition may contain cyclodextrin for higher availability. Cyclodextrin may include 100 to 1000 weights based on the effective 100 weights present in the above composition.

When measured in the third month, the above emulsion formulation is a stable form that does not show changes in the activity and solubility of wnt in distilled water under the conditions of temperature of 25° C. to 4° C. It is confirmed that the activity of the effective ingredient can be maintained for a long period of time, and absorption into the body can be effectively altered.

Another aspect of this invention is the creation of hair loss prevention or hair-promoting cosmetics, which include indirubin derivatives; and one or more selected from the group consisting of Euodia daniellii extract, Persicaria hydropiper extract, Hovenia dulcis extract, methyl vanillate, hesperidin and quercitrin; as a valid ingredient.

The indirubin derivative has little or no toxicity to cells even after long-term treatment with any one or more selected from the group consisting of Euodia daniellii extract, Persicaria hydropiper extract, Hovenia dulcis extract, methyl vanillate, hesperidin and quercitrin. When treated together, there may be any one or more selected from those represented by the following Chemical Formulas 1 to 4, which have a significant increase in effect, and preferably may be an indirubin derivative represented by Chemical Formula 1 or Chemical Formula 2. Because in vitro treatment of the indirubin derivatives and extracts of the Formula 1 or 2 together with the indirubin derivatives of the Formula 3 or 4 together with the extract and the extracts of the Formulas (1-4). This is because growth was observed in dermal papilla cells 1.5-2.5 times or more compared with the indirubin derivative treatment alone.

In addition, the above indirubin derivatives used together with any one or more selected from the group consisting of the Euodia daniellii extract, Persicaria hydropiper extract, Hovenia dulcis extract, methyl vanillate, hesperidin and quercitrin are represented by the following general Formulas 1 to 4. It may be any one or more selected from those, and most preferably may be 5,6-dichloroindirubin-3'-methoxime (Formula 2).

[Chemical formula 1]

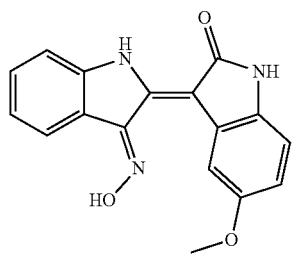

[Chemical formula 2]

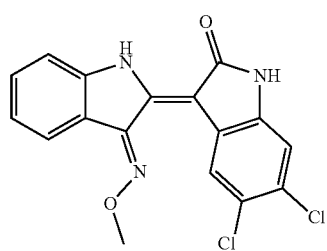

[Chemical formula 3]

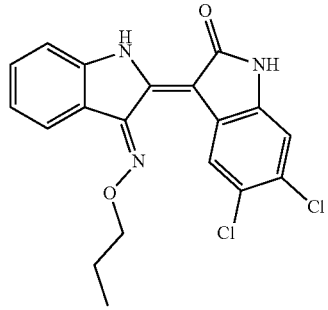

[Chemical formula 4]

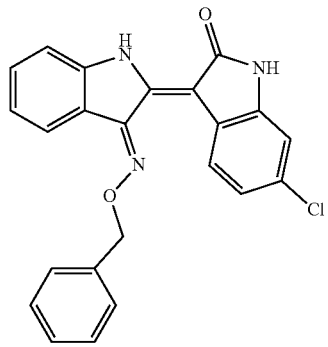

Any one or more mixed weight ratios selected from the group consisting of any one or more indirubin derivatives selected from those represented by the above Formula 1 to Formula 4, Euodia daniellii extract, Persicaria hydropiper extract, Hovenia dulcis extract, methyl vanillate, hesperidin and quercitrin is not particularly limited thereto. However, when one or more indirubin derivatives selected from the ones represented by Chemical Formulas 1 to 4 and the sheena radish extract are mixed, the indirubin derivative is based on the dry weight part 10 of the extract. Is preferably mixed in an amount of 5 to 15 parts by weight, more preferably 9 to 11 parts by weight. Outside the above range, hair loss prevention and hair promotion effects are not desirable because they degrade.

If the above composition is a mixture of indirubin derivatives represented by the formula 1 to 4 and at least one selected from methyl vanillate, hesperidin and quercitrin, any one selected from the group consisting of the methyl vanillate, hesperidin and quercitrin Although the mixing weight ratio of the above low molecular weight compound and the indirubin derivative is not particularly limited thereto, the low molecular weight compound and the indirubin derivative are preferably mixed in 1 to 20 molar ratios of the indirubin derivative based on 1 mole of the low molecular weight compound. Outside of this range, the increase of hair loss prevention and hair growth promoting effect may be insignificant.

The above extract may be extracted using a stem, a leaf, a pulverized product thereof and a mixture thereof using water, DMSO, an alcohol having 1 to 4 carbon atoms, and a mixed solvent thereof.

The above extract may be obtained by fractionating a stem, a leaf, a pulverized product thereof, and a mixture thereof with a solvent selected from the group consisting of DMSO, n-hexanoic acid, ethanol, ethyl acetate, butanol, and a mixed solvent thereof.

The above cosmetic composition not only prevents hair loss, but also has an activity for promoting hair growth.

In the cosmetic composition according to the present invention, the formulation as a cosmetic product comprising the same, in addition to the composition, a fatty substance, an organic solvent, a dissolving agent and a gelling agent, an emollient, an antioxidant, a suspending agent, a stabilizer, a foaming agent, fragrances, surfactants, radish, ionic or nonionic emulsifiers, fillers, metal ion sequestrants and chelating agents, preservatives, vitamins, blockers, wetting agents, essential oils, dyes, pigments, hydrophilic or lipophilic active agents, lipids It may contain adjuvants conventionally used in the cosmetic or dermatological field, such as vesicles or any other ingredients conventionally used in cosmetics. And the above ingredients can be introduced in amounts generally used in the field of dermatology. And the above components may be introduced in an amount generally used in the field of dermatology. Specific formulations as cosmetics of the composition of the present invention include skin lotion, skin softener, skin toner, astringent, lotion, milk lotion, moisturizing lotion, nutrition lotion, massage cream, nutrition cream, moisture cream, hand cream, essence, nutrition essence, Formulations include packs, soaps, shampoos, cleansing foams, cleansing lotions, cleansing creams, body lotions, body cleansers, emulsions, press powders, loose powders, eye shadows and the like.

However, the composition of the present invention can be used by a method such as applying or spreading directly on the hair or scalp. The hair to which the extract of the present invention is applied includes all parts of the hair root and hair follicles, such as the hair root and hair follicle of the head, and the overall hair.

Therefore, the cosmetic composition of the present invention is most preferably any one hair formulation selected from the group consisting of shampoo, spray, rinse, hair gel, hair tonic, hair lotion, soap or hair pack.

The cosmetic composition of the present invention provides a cosmetic composition useful for preventing and treating hair loss by preventing hair follicles from entering the telogen phase, maintaining the anagen phase, preventing hair loss, and promoting hair growth.

The formulation of the cosmetic composition according to the present invention may preferably be an emulsion formulation further comprising an oil, a surfactant and polyethylene glycol.

In the above emulsion formulation, the mixed weight ratio of the above oil, surfactant and polyethylene glycol may be 0.3-30:1:2-2.5, more preferably 10-20:1:2-2.5. The composition of the emulsion formulation may be determined by a similar three-phase diagram drawn according to conventional methods of determining the composition of the emulsion system. Specifically, the oil phase (polyethoxylated castor oil (Kolliphor® EL)) and the surfactant (eg a mixture of tween 80 and polyethylene glycol) are thoroughly mixed in different weight ratios in a specific ratio range. The pseudo-three phase diagram can then be created by adding water to each proportion of the oil and surfactant mixture and marking the points corresponding to the emulsion forming region. By determining the emulsion region from a similar three-phase diagram prepared, the key to the above validity (a mixture of one or more selected compounds from a group of indirubin derivatives and Euodia daniellii extract, Persicaria hydropiper extract, Hovenia dulcis extract, methyl vanillate, hesperidin and quercitrin) can be determined as a melting emulsion.

If the composition is an emulsion formulation, any one or more selected from the group consisting of the active ingredient (indirubin derivatives and Euodia daniellii extract, persicaria hydropiper extract, hovenia dulcis extract, methyl vanillate, hesperidin and quercitrin are mixed Compound) is preferably included 1 to 20% by weight based on the total weight of the composition.

The surfactant serves as a co-solvent as a twin-based nonionic surfactant, and is used as an emulsifier or wetting agent in oral or parenteral preparations in pharmaceuticals, and as an additive in cosmetics or foods. It is also used as a substance for inhibiting p-glycoprotein to increase the bioavailability of the drug. Tween-based surfactants include polyoxyethylene sorbitan monolaurate (Tween 20), polyoxyethylene sorbitan monopalmitate (Tween 40), polyoxyethylene sorbitan monostearate (polyoxyethylene sorbitan monostearate, Tween 60) and polyoxyethylene sorbitan oleate (Tween 80), but not limited to any one or more selected from the group consisting of. The above Twin series of surfactants is a stable substance licensed by the U.S. Food and Drug Administration for use in intravenous injections of the human body.

In addition, the above polyethylene glycol is a two-sided polymer with hydrophobic and hydrophobic properties, which is a liquid at low molecular weight, but becomes solid as the molecular weight increases. The polyethylene glycol above may be used either of the selected polyethylene glycols from a group of PEG 150, 300, 400, 1000, 6000, 8000, 10000, 20000, 30000 and 40000 which means polyethylene glycol with a molecular weight exceeding 10,000 is also referred to as polyethylene oxide (PEO). Among these, PEG400 exists in the form of liquids, is frequently used in the availability of various insoluble drug water, and is a sedate substance authorized by the Food and Drug Administration (FDA) to use the human body's oral and non-vascular (IV injection, subcutaneous injection, muscle injection, etc.).

The surfactant used in the embodiments of this invention is polyoxyethylene sorbitan oleate (Tween 80), polyethylene glycol is PEG 400, which has paternal and non-ionic properties and is distributed in water. This emulsion molding can be provided optimized for insoluble efficacy (a compound of one or more selected from a group of Euodia daniellii extract, Persicaria hydropiper extract, Hovenia dulcis extract, methyl vanillate, hesperidin and quercitrin).

The above oil may be one or more selected from a group of polyetoxylated pyjamasyl(Kolliphor® EL), sunflower oil and olive oil.

The above composition may contain cyclodextrin for higher availability. Cyclodextrin may include 100 to 1000 weights based on the effective 100 weights present in the above composition.

When measured in the third month, the above emulsion formulation is a stable form that does not show changes in the activity and solubility of wnt in distilled water under the conditions of temperature of 25° C. to 4° C. It is confirmed that the activity of the effective ingredient can be maintained for a long period of time, and absorption into the body can be effectively altered.

Another aspect of this invention is about hair promoting products, comprising indirubin derivatives; and one or more selected from group consisting of Euodia daniellii extract, Persicaria hydropiper extract, Hovenia dulcis extract, methyl vanillate, hesperidin and quercitrin as an effective component.

The above health-functioning food shall be a combination of the above Indirubin derivatives and one or more of the following compounds, including Euodia daniellii extract, Persicaria hydropiper extract, Hovenia dulcis extract, methyl vanillate, hesperidin and quercitrin, formulated as form of capsule, tablet, powder, granules, liquid form, pill, particle, paste, syrup, gel, jelly or bar. or added to food ingredients such as beverages, teas, spices, chewing gum, and confectionery, which means they have a health-specific effect when ingested, but unlike ordinary medicines, they have no side effects that can be generated during long-term use of the drug.

The above health-related foods are very useful because they are available on a daily basis. The above Indirubin derivatives in these health function foods; the addition of compounds containing one or more of the above, including Euodia daniellii extract, Persicaria hydropiper extract, Hovenia dulcis extract, methyl vanillate, hesperidin and quercitrin, shall not be uniformly specified depending on the type of health function food to which the food is not intended to be eaten in a range of 0.1% or 20%. In addition, for health functioning foods in the form of capsule, tablet, powder, granules, liquid form, pill, particle, paste, syrup, gel, jelly or bar, they shall normally be added in the range of 80 percent of weight within 0.5.

The above health function food, as a valid ingredient, may contain ingredients that are commercially added in the manufacture of food, for example protein, carbohydrates, fats, fats, nutrients, and flavoring agents, as well as any of the ingredients selected from the group consisting of the above indirubin derivatives and Euodia daniellii extract, Persicaria hydropiper extract, Hovenia dulcis extract, methyl vanillate, hesperidin and quercitrin. Examples of the above carbohydrates are monocarides, e.g. glucose, fructose, etc.; decaccharides, e.g. maltose, sucrose, oligosaccharides etc.; and glycosaccharides, such as dextrin, cyclodextrin, etc., and glycols such as xylitol, sorbitol, and erythritol.

Natural flavouring agents [towmatins, stevia extracts (e.g. le boudiocide A, glycirrhizine, etc.) and synthetic flavouring agents (sakarin, aspartame, etc.) may be used as flavouring agents. For example, if the health-functioning food of this invention is manufactured from drinks and beverages, it may additionally include citric acid, liquid sugar, sugar, glucose, herbic acid, apple acid, nectar, and various plant extracts.

We intend to explain this invention in more detail by embodiment, but the scope and contents of this invention cannot be construed as being reduced or restricted by embodiment. Based on the initiation of this invention, including the following embodiment, it is clear that the ordinary technician can easily carry out this invention, which has not been specifically tested. No wonder these variations and modifications fall within the scope of the patent claims attached.

In addition, the results of the experiments presented below are representative of the results of the embodiments and the comparative examples. The effects of each of the different implementations of this invention, not explicitly presented below, are detailed in that section.

Manufacturing example 1. Synthesis of 5-methoxyindirubin-3'-oxime (A3334)

① Synthesis of Intermediate Product, 5'-methoxy-[2,3'-biindolinylidene]-2',3-dione

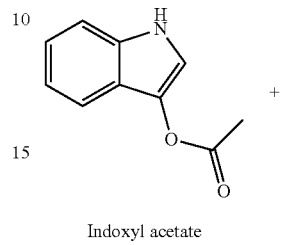

Indoxyl acetate

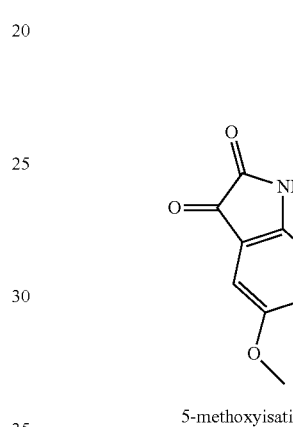

5-methoxyisatin

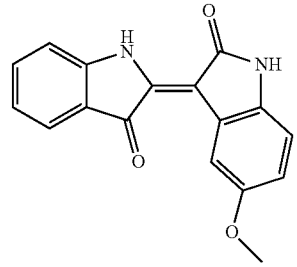

5'-methoxy-[2,3'-biindolinylidene]-2',3-dione 5-methoxyisatin (1000 mg, 5.65 mmol) was added to a 250-mL round bottom flask and dissolved in methanol (225 mL), followed by the addition of indoxyl acetate (989 mg, 5.65 mmol) and sodium carbonate (Na2CO3) (1496 mg, 14.11 mmol), and the mixture is stirred at 65° C. for 12 hours. The reaction is terminated using TLC (Rf=0.4, ethyl acetate/hexane=1/2 (v/v)) and the product is allowed to cool down on ice until a lump of crystals is formed. After the crystals are formed and the solvent is removed by filtration, the filtrate is discarded, and the product is washed several times with a solvent (ethanol/water=1/1 (v/v)). The product was filtered and dried in a vacuum pump and used in the next step without further purification.

② Synthesis of A3334

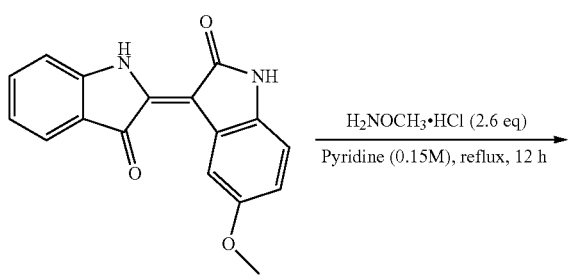

5'-methoxy-[2,3'-biindolinylidene]-
2',3-dione

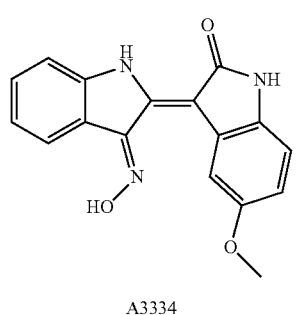

A3334

5'-methoxy-[2, 3'-biindolinylidene]-2', 3-dione) (670 mg, 2.29 mmol) was added to a 100-mL round bottom flask and dissolved in pyridine (27 ml), followed by addition of H2NOCH3·HCl (3186 mg, 45.85 mmol) and the mixture was stirred at 120° C. for 12 hours. The reaction is terminated using TLC (Rf=0.5, ethyl acetate/hexane=1/1 (v/v)) and the temperature of the reaction solution is lowered to room temperature. After evaporation of the pyridine solvent, the product was dissolved in water and ethylacetate for 30 minutes using ultrasonic waves. The product was extracted twice with ethyl acetate and washed with saturated NaHCO$_3$ solution. The extracted solution is dehydrated with anhydrous magnesium sulfate, the solvent is evaporated and recrystallized using methanol and nucleic acid. The product was dried in a vacuum pump and red solid A3334 can be obtained (420 mg) in 59% yield. 1H NMR (400 MHz, DMSOd6) δ 13.52 (s, 1H), 11.79 (s, 1H), 10.54 (s, 1H), 8.35 (d, J=1.5 Hz, 1H), 8.26 (d, J=7.6 Hz, 1H), 7.41 (d, J=2.8 Hz, 2H), 7.08-7.00 (m, 1H), 6.82-6.71 (m, 2H), 3.78 (s, 3H).

Manufacturing Example 1. Synthesis of 5, 6-dichloroindirubin-3'-methoxime (A3051)

① Synthesis of Intermediate Product, 5',6'-dichloro-[2,3'-biindolinylidene]-2',3-dione

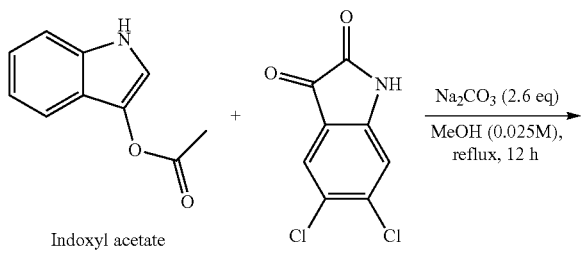

Indoxyl acetate    5,6-dichloroisatin

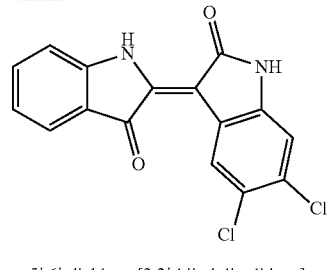

5',6'-dichloro-[2,3'-biindolinylidene]-
2',3-dione 5,6-dichloroisatin (500 mg, 2.32 mmol) was added to a 250 mL round bottom flask and dissolved in methanol (MeOH) (92.80 mL) followed by the addition of indoxyl acetate (405.48 mg, 2.315 mmol) and sodium percarbonate (Na2CO3) (637.83 mg, 6.02 mmol), and the mixture was stirred at 65° C. for 12 hours. The reaction is terminated using TLC (Rf=0.4, ethyl acetate/hexane=1/2 (v/v)) and the product is allowed to cool down on ice until a lump of crystals is formed. After the crystals are formed, the solvent is removed by filtration. The filtrate is discarded and the product is washed several times with a solvent (ethanol/water=1/1 (v/v)). The product was filtered and dried in a vacuum pump and used in the next step without further purification.

② Synthesis of A3051

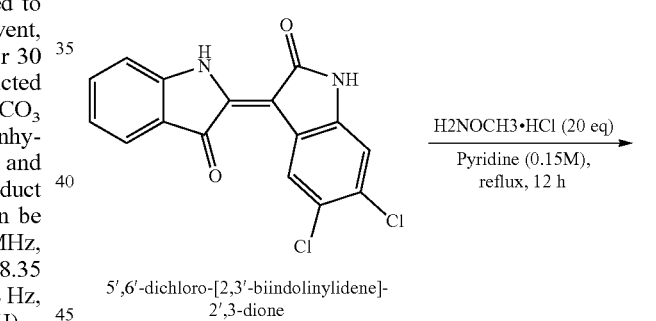

5',6'-dichloro-[2,3'-biindolinylidene]-
2',3-dione

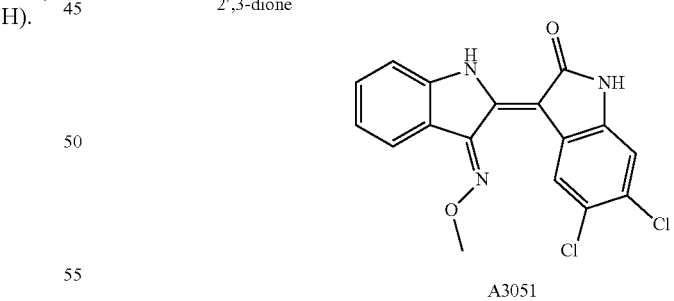

A3051

A 100 ml round-bottomed flask was charged with 5', 6'-dichloro-[2,3'-biindolinylidene]-2',3-dione (600 mg, 1.81 mmol) and it was dissolved in pyridine (151 ml), and then H2NOCH3·HCl (3026.4 mg, 36.24 mmol) was added, and the mixture was stirred at 120° C. for 12 hours. The reaction is terminated using TLC (Rf=0.4, ethyl acetate/hexane=1/1 (v/v)) and the temperature of the reaction solution is lowered to room temperature. After evaporation of the pyridine solvent, the product was dissolved in water and ethylacetate for 30 minutes using ultrasonic waves. The product was extracted twice with ethyl acetate and washed with saturated NaHCO$_3$ solution. The extracted solution is dehydrated with anhydrous magnesium sulfate, and the solvent is evaporated and recrystallized using methanol and nucleic acid. The product was dried in a vacuum pump and red solid A3051 (326 mg) can be obtained in 47.94% yield. 1H NMR (400 MHz, DMSO-d6) δ 11.36 (s, 2H), 8.80 (s, 1H), 8.08 (d, 1H, J=7.7 Hz), 7.46-7.41 (m, 2H), 7.07-6.99 (m, 2H), 4.38 (s, 3H).

Manufacturing Example 3 & 4. Manufacturing of Indirubin Derivative, Formula 3 (A3486) and Formula 4 (A3538)

5,6-dichloroindirubin-3'-oximepropyloxime of formula 3 and 6-chloroindirubin-3'-benzyloxime of formula 4 are synthesized in the same method with 5,6-dichloroindirubin-3'-methoxime or 5-methoxylindiruvin-3'-oxime, which was dissolved in dimethyl sulfide (DMSO) and applied to the experiment.

Manufacturing Example 5. Manufacturing Euodia Daniellii Extract

Euodia daniellii extract for the experiment was purchased from the Korea Plant Extract Bank, briefly crushed (1~3 mm) stems and leaves of Euodia daniellii tree, prepared by washing it in distilled water, and then extracted with 80% ethanol and concentrated by using Speed var concentrator. After the extraction was completed, each extract were powdered by freeze drying at −70° C.

The powder of Euodia daniellii extract was dissolved in dimethyl sulfide (DMSO) at a concentration of 1 μg/ml and used for the experiment.

Manufacturing Example 5. Manufacturing Persicaria Hydropiper Extract

Persicaria hydropiper extract for the experiment was purchased from the Korea Plant Extract Bank, briefly crushed (1~3 mm) stems and leaves of Persicaria hydropiper, prepared by washing it in distilled water, and then extracted with 80% ethanol and concentrated by using Speed var concentrator. After the extraction was completed, each extract were powdered by freeze drying at −70° C.

The powder of Persicaria hydropiper extract was dissolved in dimethyl sulfide (DMSO) at a concentration of 1 μg/ml and used for the experiment.

Manufacturing Example 5. Manufacturing Hovenia Dulcis Extract

Hovenia dulcis extract for the experiment was purchased from the Korea Plant Extract Bank, briefly crushed (1~3 mm) stems and leaves of Hovenia dulcis, prepared by washing it in distilled water, and then extracted with 80% ethanol and concentrated by using Speed var concentrator. After the extraction was completed, each extract were powdered by freeze drying at −70° C.

The powder of Hovenia dulcis extract was dissolved in dimethyl sulfide (DMSO) at a concentration of 1 μg/ml and used for the experiment.

Manufacturing Example 8. Preparing Methyl Vanillate

Methyl vanillate was purchased from Sigma Aldrich.

Manufacturing Example 9. Preparing Hesperidin

Hesperidin was purchased from Sigma Aldrich.

Manufacturing Example 10. Preparing Quercitrin

Quercitrin was purchased from Sigma Aldrich.

Embodiment 1. Compound Euodia Daniellii Extract with Indirubin Derivative (A3334; Formula 1)

To identify hair loss prevention and hair growth promoting effect, a composite was prepared by mixing the Euodia daniellii extract of manufacturing Example 5 and the indirubin derivative represented by Formula 1 (A3334), respectively, 1 μg/ml and 0.1 μM.

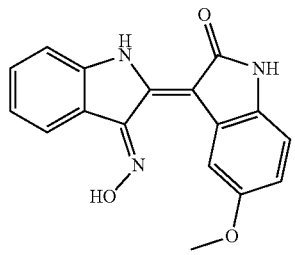

[Formula 1]

Embodiment 2. Compound Euodia Daniellii Extract with Indirubin Derivative (A3051: Formula 2)

To identify effect of preventing hair loss and promoting hair growth, a composite was prepared by mixing the Euodia daniellii extract of manufacturing Example 5 and the indirubin derivative represented by Formula 2 (A3051), respectively, 1 μg/ml and 0.1 μM.

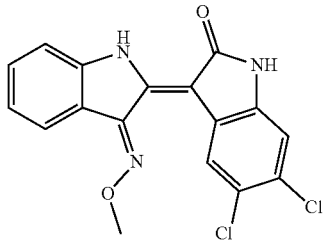

[Formula 2]

Embodiment 3. Compound Euodia Daniellii Extract with Indirubin Derivative (A3486; Formula 3)

To identify effect of preventing hair loss and promoting hair growth, a composite was prepared by mixing the Euodia daniellii extract of manufacturing Example 5 and the indirubin derivative represented by Formula 3 (A3486), respectively, 1 μg/ml and 0.1 μM.

Embodiment 4. Compound Euodia Daniellii Extract with Indirubin Derivative (A3538; Formula 4)

To identify effect of preventing hair loss and promoting hair growth, a composite was prepared by mixing the Euodia daniellii extract of manufacturing Example 5 and the indirubin derivative represented by Formula 4 (A3538), respectively, 1 µg/ml and 0.1 µM.

Embodiment 5. Compound Persicaria Hydropiper Extract with Indirubin Derivative (A3051; Formula 2)

To identify effect of preventing hair loss and promoting hair growth, a composite was prepared by mixing the Persicaria hydropiper extract of manufacturing Example 6 and the indirubin derivative represented by Formula 2 (A3051), respectively, 1 µg/ml and 0.1 µM.

Embodiment 6. Compound Hovenia Dulcis Extract with Indirubin Derivative (A3051; Formula 2)

To identify effect of preventing hair loss and promoting hair growth, a composite was prepared by mixing the Hovenia dulcis extract of manufacturing Example 7 and the indirubin derivative represented by Formula 2 (A3051), respectively, 1 µg/ml and 0.1 µM.

Embodiment 7. Compound Methyl Vanillate with Indirubin Derivative (A3051; Formula 2)

A composite was prepared by mixing the methyl vanillate of manufacturing Example 8 and the indirubin derivative represented by Formula 2 (A3051), respectively, 1 µM and 5 µM.

Embodiment 8. Manufacturing of Compound Hesperidin with Indirubin Derivative

A composite was prepared by mixing the hesperidin of manufacturing Example 9 and the indirubin derivative represented by Formula 2 (A3051), respectively, 0.1 µM and 1 µM.

Embodiment 9. Manufacturing of Compound Quercitrin with Indirubin Derivative

A composite was prepared by mixing the quercitrin of manufacturing Example 10 and the indirubin derivative represented by Formula 2 (A3051), respectively, 0.1 µM and 1 µM.

Experimental Example 1. Proliferative Effect of Dermal Papilla Cells

The purpose of this study was to identify ALP (alkaline phosphatase) activity, a marker that indicates hair growth promotion in human dermal papilla cells, by the complex of embodiments 1-4.

The dermal papilla cells were distributed from Kyungpook National University (Korea), and the dermal papilla cells of 0.5×105 were dispensed into 24 well plates, and then cultured under 37° C. and 5% CO 2. The medium was incubated in DMEM medium containing 10% FBS and antibiotics (penicillin streptomycin). After culturing up to 1 day cells were stably attached, the complexes of embodiments 1 to 4 were added to the respective media by concentration (0 µM, 0.1 µM to 1 µM, 0.5 µM to 5 µM). After 48 hours, the culture medium was removed, cells were collected by adding lysis buffer, and the supernatant was recovered by centrifugation (13000 rpm, 15 minutes, 4). 30 µl of the supernatant and 30 µl of PNPP solution were added to a 96 well plate, incubated for 1 hour, and then absorbance was measured at 405 nm. ALP activity was quantified by measuring protein concentration using the Bradford assay.

FIG. 1a is a graph showing the quantitative measurement of ALP (alkaline phosphatase) activity according to the treatment of the compound prepared from embodiment 2 in human dermal papilla cells.

Figure 1B:
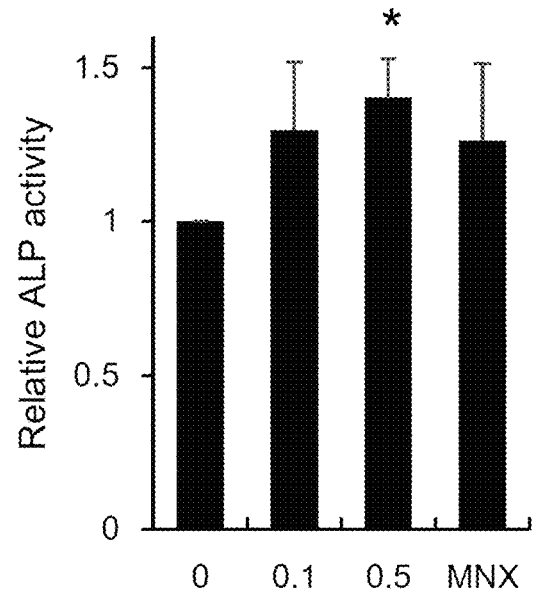
FIG. 1b is a graph showing the measurement of the alkaline phosphatase (ALP) activity following the treatment of the complex prepared from Embodiment 1 in human dermal papilla cells.
Figure 1C:
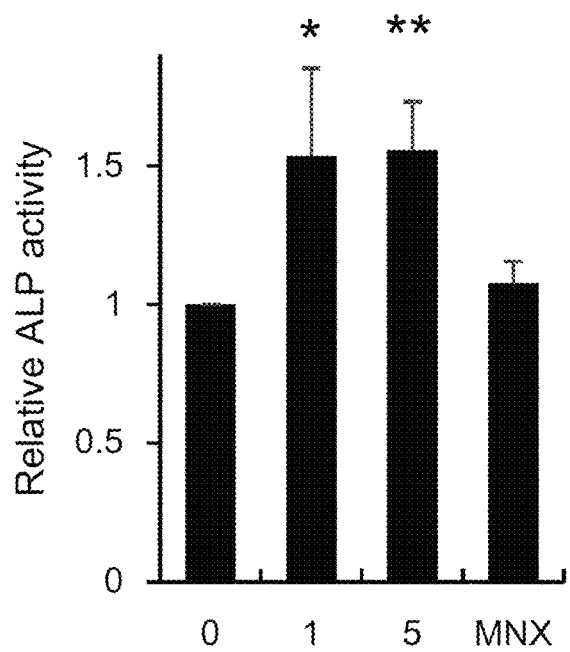
FIG. 1c is a graph showing the measurement of the alkaline phosphatase (ALP) activity following the treatment of the complex prepared from Embodiment 3 in human dermal papilla cells.
Figure 1D:
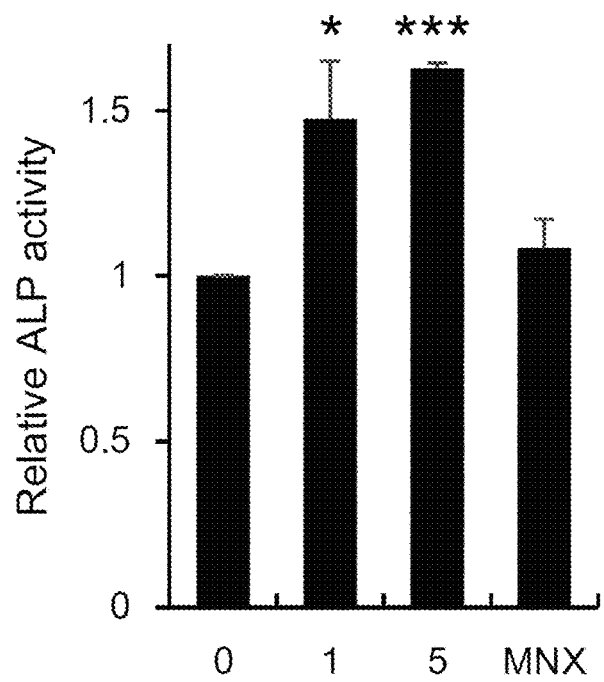
FIG. 1d is a graph showing the measurement of the alkaline phosphatase (ALP) activity following the treatment of the complex prepared from Embodiment 4 in human dermal papilla cells. Minoxidil (MNX), a conventional hair loss treatment, was used as positive control.

FIG. 1b is a graph showing the measurement of ALP (alkaline phosphatase) activity according to the treatment of the compound prepared from embodiment 1 in human dermal papilla cells, FIG. 1c is a graph showing the measurement of ALP (alkaline phosphatase) activity according to the treatment of the compound prepared from embodiment 3 in human dermal papilla cells, FIG. 1d is a graph showing the measurement of ALP (alkaline phosphatase) activity according to the treatment of the compound prepared from Embodiment 4 in human dermal papilla cells. The positive control (MNX) was minoxidil, a conventional hair loss treatment drug.

Embodiment 1 and 4 according to the present invention, all ALP activity were significantly increased.

This is 1.5 times higher than the positive control group (MNX) and negative control group (O µM), which indicates that it is more significant than the conventional hair loss treatment (minoxidil).

In addition, ALP activity similar to the negative control (0 µM) was observed when the Euodia daniellii extract and indirubin derivatives (manufacturing Example 1-4) were treated alone (not shown), it was found that combination treatment with an appropriate dose (1:1) have a higher effect than its expected synergistic effect.

Measurement of Hair Growth Efficacy of the Compounds Prepared from Embodiments 1-4 in Ex Vivo.

1) Isolation and Culture of Vibrissa Follicles from Mouse

After sacrificing 6 to 8 weeks old male mice, the tissues around the mouth are removed, soaked in 70% ethanol solution once, and then placed in PBS containing 1% P/S. By using a microscope, the early anagen vibrissa follicles were carefully separated one by one and placed in PBS containing 1% P/S. When the separation is completed, put one follicle into 24 well plates in each medium containing the sample (DMEM serum free 1% P/S+62.5 µg/ml gentamicin), and then incubated in 37° C., 5% CO 2 incubator. 8-12 hair follicles were used in one experimental group, and the culture medium was changed every two days. Cultures were observed on a dissecting microscope at day 6.

At this time, the sample is a single substance (indirubin derivative, Euodia daniellii extract alone) prepared from manufacturing Examples 1 to 5, respectively; or composite prepared from Embodiments 1-4.

2) Measurement of Growth of Mouse Nose Hair Shaft 6 to 8 weeks of age, nasal hair follicles were isolated and cultured for 6 days. The hair shaft length was measured while examining whether the composite prepared from Embodiment 1 to 4 had hair growth efficacy.

Nose hair follicle morphology in culture was photographed using a microscope (SMZ745T, Nikon). Hair follicle length was measured using image J. The average value of the hair follicle length change was calculated and compared with the average length of the control group.

Figure 2A:
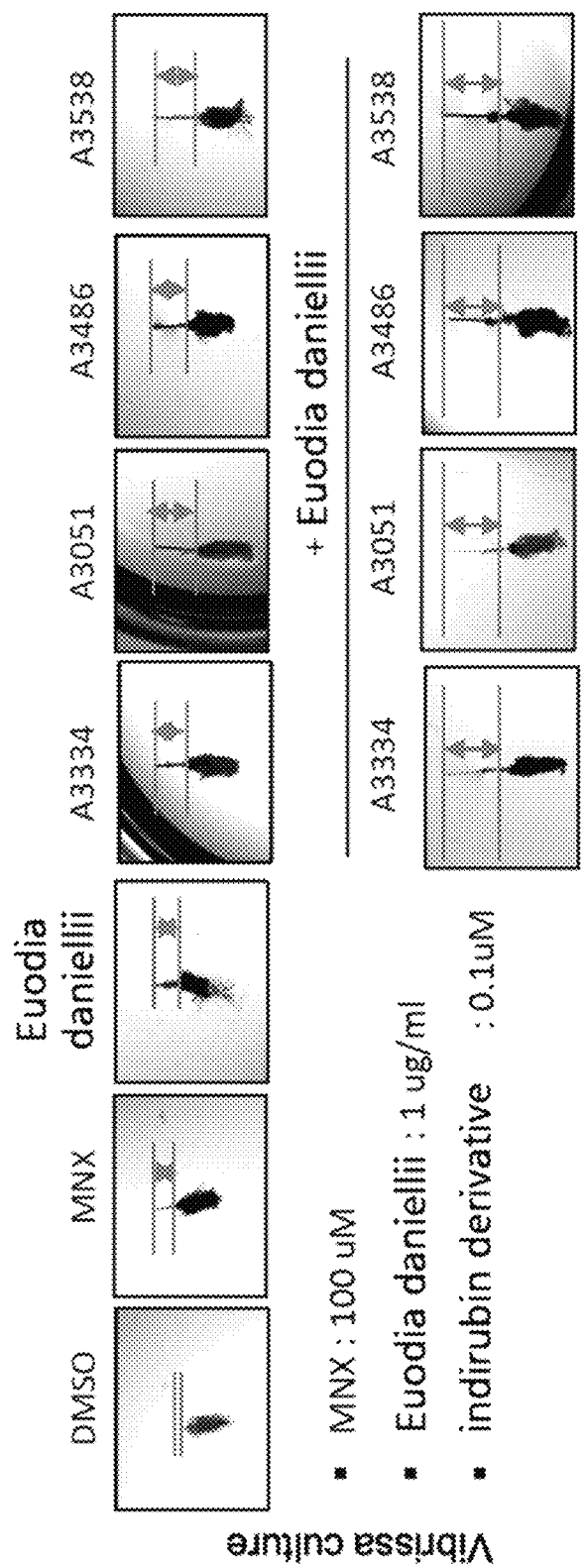
FIG. 2a is a photograph taken under a microscope showing the effect on promoting hair shaft growth in each experimental group when a single substance prepared from manufacturing Examples 1 to 5 (indirubin derivatives, Euodia daniellii extract alone) or the complexes prepared from Embodiment 1 to 4 were treated in mouse vibrissa follicles.

FIG. 2a is a micrograph showing the hair shaft growth promoting effect in the experimental group when single substance prepared from manufacturing Examples 1 to 5 (indirubin derivatives, Euodia daniellii extract alone), the composites prepared from Embodiments 1 to 4, respectively are treated on mouse nose hair follicles (vibrissa follicles).

Figure 2B:
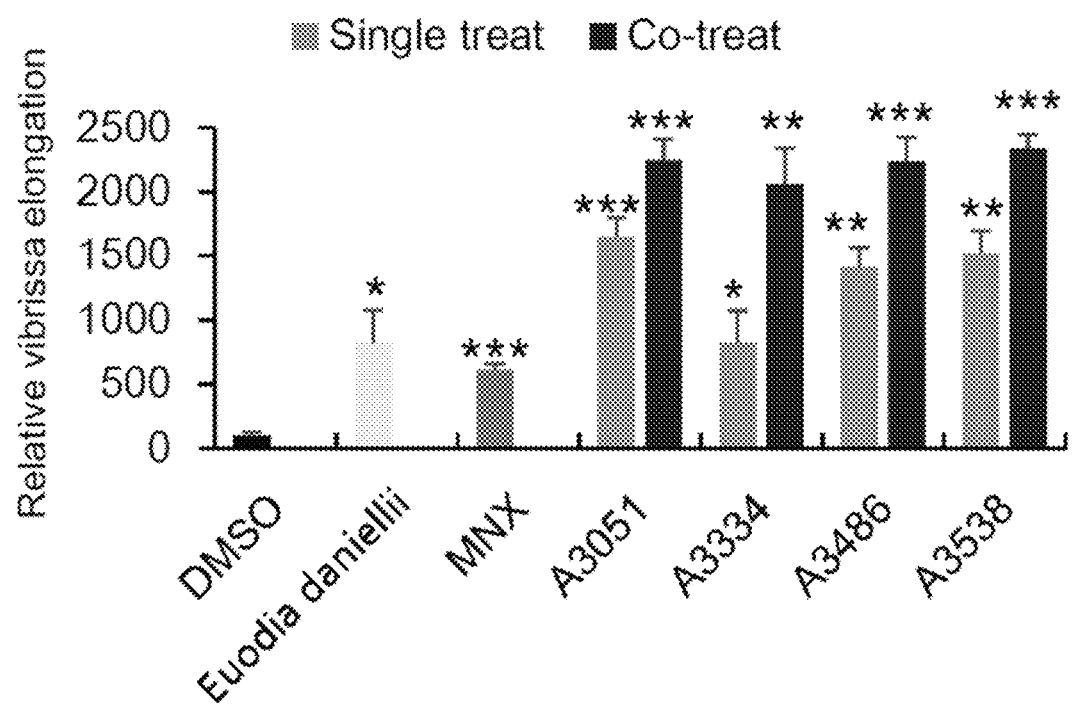
FIG. 2b is a graph showing the statistical analyses of changes in the length of hair shaft growth in each experimental group when a single material (Indirubin derivatives, Euodia daniellii extract alone) prepared from manufacturing Examples 1 to 5 or the composites prepared from Embodiment 1 to 4 were treated in mouse vibrissa follicles (data are expressed as mean±SD and * $P<0.05$,  $P<0.005$, * $P<0.0005$ vs. control).

FIG. 2b is a graph showing the change in the length of hair shaft growth in the experimental group when single substance prepared from manufacturing Examples 1 to 5 (indirubin derivatives, Euodia daniellii extract alone), the composites prepared from Embodiments 1 to 4, respectively, are treated on mouse nose hair follicles (vibrissa follicles). (data are expressed as mean, SD and * P<0.05,  P<0.005, * P<0.0005 vs. control).

As shown in FIG. 2, it was confirmed that the composite of Euodia daniellii extract and indirubin derivatives significantly improved the hair fiber length of mouse nose hair follicles. Specifically, compared to the case of using the indirubin derivatives of the manufacturing examples 1 to 5 and the Euodia daniellii extract alone (single treat), the case of using the composite of embodiments (co-treat) 1 to 4 have 1.6 to 2.5 times higher effect. It was a significant increase of effect which was not expected when the indirubin derivatives were used alone or when the Euodia daniellii extract was used alone.

Therefore, it is found that the composite prepared from Embodiments 1 to 4 of the present invention can be used as a composition useful for preventing hair loss and promoting hair growth.

Experimental Example 3. Measurement of Hair Growth Efficacy of the Composite Prepared from Embodiments 5 to 6 in Ex Vivo 1) Isolation and Culture of Vibrissa Follicles from Mouse After sacrificing 6 to 8 weeks old male mice, the tissues around the mouth are removed, soaked in 70% ethanol solution once, and then placed in PBS containing 1% P/S. By using a microscope, the early anagen vibrissa follicles were carefully separated one by one and placed in PBS containing 1% P/S. When the separation is completed, put one follicle into 24 well plates in each medium containing the sample (DMEM serum free 1% P/S+62.5 µg/ml gentamicin), and then incubated in 37° C., 5% CO 2 incubator. 8-12 hair follicles were used in one experimental group, and the culture medium was changed every two days. Cultures were observed on a dissecting microscope at day 6.

At this time, the sample is a single substance (indirubin derivative, Persicaria hydropiper extract, Hovenia dulcis extract) prepared from manufacturing Examples 2, 6, 7, respectively; or composite prepared from Embodiments 5, 6.

Minoxidil (MNX) 100 µM was used as a positive control and DMSO was used as a vehicle control.

2) Measurement of Growth of Mouse Nose Hair Shaft 6 to 8 weeks of age, vibrissa follicles were isolated and cultured for 6 days. The hair shaft length was measured while examining whether the composite prepared from Embodiment 5, 6 had hair growth efficacy.

Nose hair follicle morphology in culture was photographed using a microscope (SMZ745T, Nikon). Hair follicle length was measured using image J. The average value of the hair follicle length change was calculated and compared with the average length of the control group.

Figure 3A:
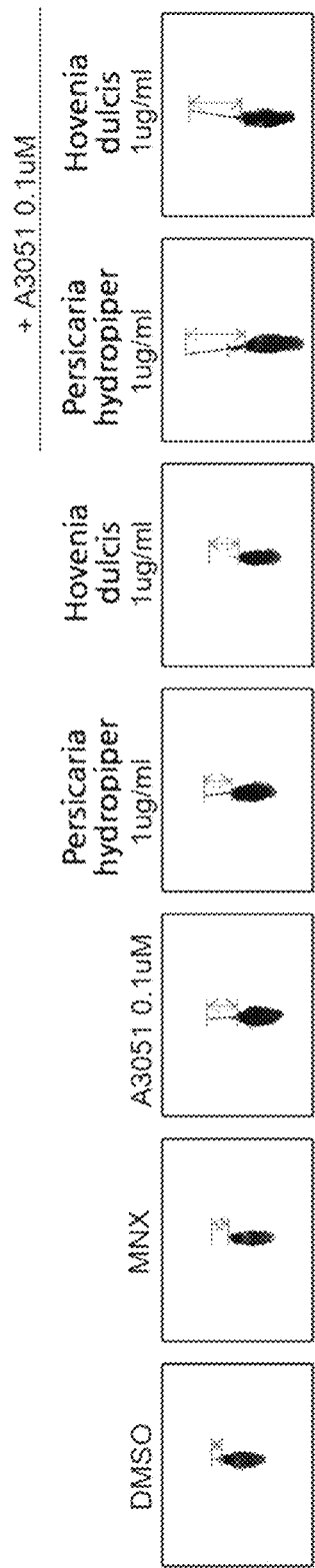
FIG. 3a is a photograph taken under a microscope showing the effect on promoting hair shaft growth in each experimental group when treated with a composite prepared from manufacturing Examples 2, 6, 7 (indirubin derivatives, Persicaria hydropiper extracts, Hovenia dulcis extracts alone) or the complexes prepared from Embodiments 5, 6 in mouse vibrissa follicles.

FIG. 3a is a photograph showing the hair shaft growth promoting effect in the experimental group when single substance prepared from manufacturing Examples 2, 6, 7 (indirubin derivatives, Persicaria hydropiper extract, Hovenia dulcis extract alone), the composites prepared from Embodiments 5, 6 respectively are treated on mouse vibrissa follicles.

Figure 3B:
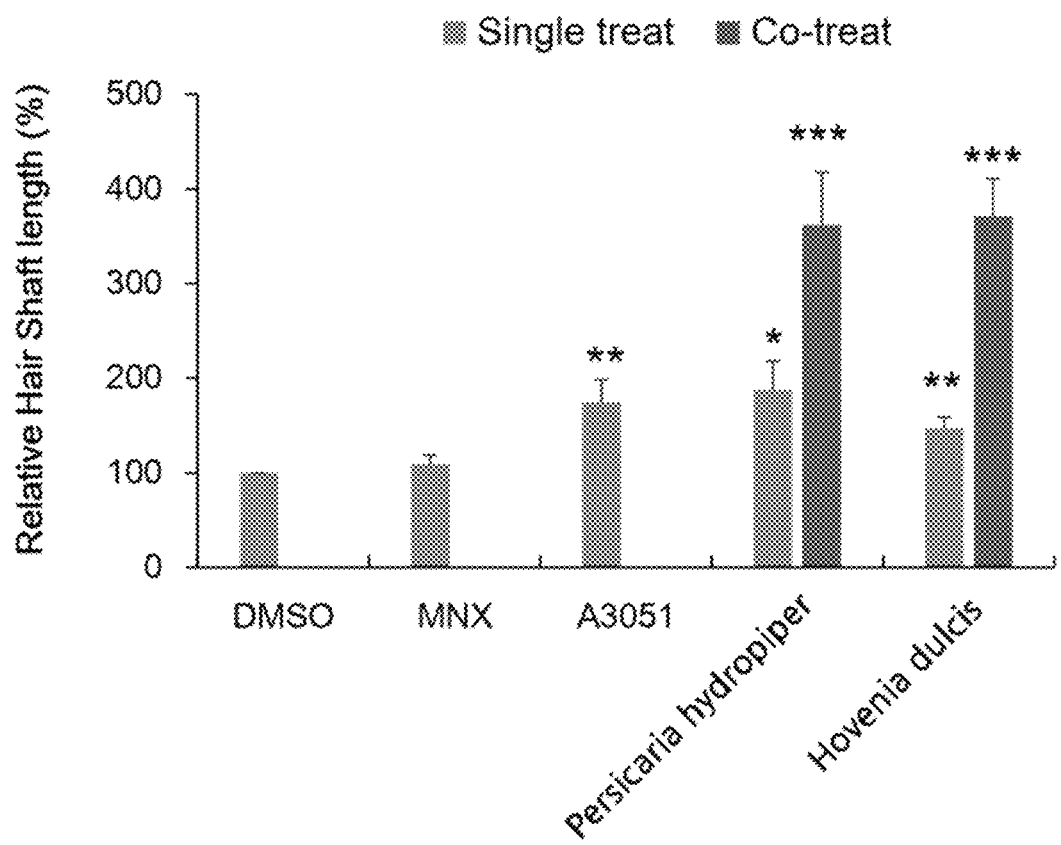
FIG. 3b is a graph showing the statistical analyses for change in hair shaft growth length in each experimental group when treated with a composite prepared from manufacturing Examples 2, 6, and 7 (indirubin derivatives, Persicaria hydropiper extracts, Hovenia dulcis extracts alone) or the complexes prepared from Embodiments 5 and 6 in mouse vibrissa follicles (data is expressed as mean±SE, and * $P<0.05$,  $P<0.005$, * $P<0.0005$ vs. control).

FIG. 3b is a graph showing the change in the length of hair shaft growth in the experimental group when single substance prepared from manufacturing Examples 2, 6, 7 (indirubin derivatives, Persicaria hydropiper extract, Hovenia dulcis extract alone), the composites prepared from Embodiments 5, 6, respectively, are treated on mouse nose hair follicles (vibrissa follicles). (data are expressed as mean, SD and * P<0.05,  P<0.005, * P<0.0005 vs. control).

As shown in FIG. 3, it was confirmed that the composite of Persicaria hydropiper extract or Hovenia dulcis extract and indirubin derivatives significantly improved the hair fiber length of mouse nose hair follicles. Specifically, compared to the case of using the indirubin derivatives of the manufacturing examples 2, 6, 7 and the extract alone (single treat), the case of using the composite of embodiments (co-treat) 5, 6 have 2 times higher effect. It was a significant increase of effect which was not expected when the indirubin derivatives were used alone or when the Persicaria hydropiper extract or Hovenia dulcis extract was used alone.

Therefore, it is found that the composite prepared from Embodiments 5, 6 of the present invention can be used as a composition useful for preventing hair loss and promoting hair growth.

Experimental Example 4. Measurement of Hair Growth Efficacy of the Composite Prepared from Embodiments 2, 7, 9 in Ex Vivo 1) Isolation and Culture of Vibrissa Follicles from Mouse After sacrificing 6 to 8 weeks old male mice, the tissues around the mouth are removed, soaked in 70% ethanol solution once, and then placed in PBS containing 1% P/S. By using a microscope, the early anagen vibrissa follicles were carefully separated one by one and placed in PBS containing 1% P/S. When the separation is completed, put one follicle into 24 well plates in each medium containing the sample (DMEM serum free 1% P/S+62.5 µg/ml gentamicin), and then incubated in 37° C., 5% CO 2 incubator. 8-12 hair follicles were used in one experimental group, and the culture medium was changed every two days. Cultures were observed on a dissecting microscope at day 6.

At this time, the sample is a single substance (indirubin derivative, Euodia daniellii extract, methyl vanillate, hesperidin, quercitrin alone) prepared from manufacturing Examples 2, 5, 8, 10 respectively; or composite prepared from Embodiments 2, 7, 9.

Minoxidil (MNX) (100 µM) was used as a positive control and DMSO was used as a vehicle control.

2) Measurement of Growth of Mouse Nose Hair Shaft 6 to 8 weeks of age, nasal hair follicles were isolated and cultured for 6 days. The hair shaft length was measured while examining whether the composite prepared from Embodiment 2, 7, 9 had hair growth efficacy.

Nose hair follicle morphology in culture was photographed using a microscope (SMZ745T, Nikon). Hair follicle length was measured using image J. The average value of the hair follicle length change was calculated and compared with the average length of the control group.

Figure 4:
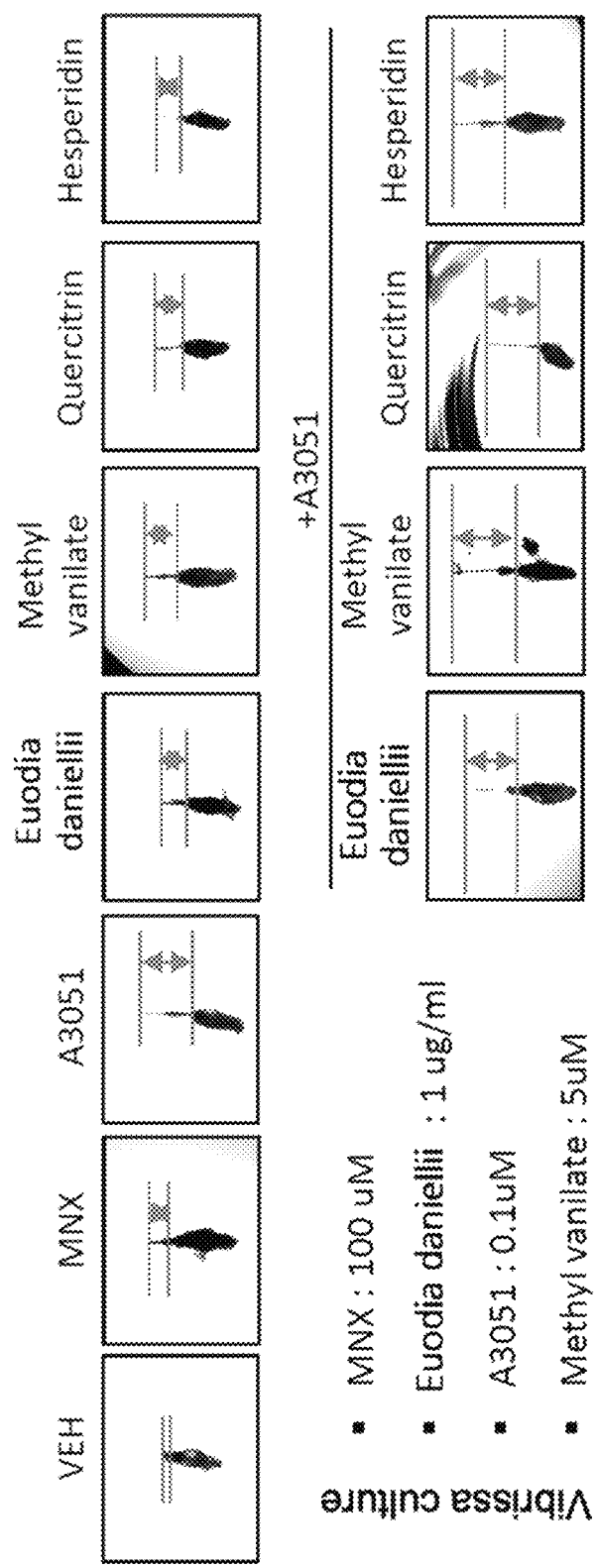
FIG. 4 is a photograph showing the hair shaft growth promoting effect in each experimental group when treated with a composite prepared from the manufacturing examples 2, 5, 8 to 10 (indirubin derivative, Euodia daniellii extracts. methyl vanillate, hesperidin, quercitrin alone) or the complexes prepared from Embodiments 2 and 7 to 9.

FIG. 4 is a photograph showing the hair shaft growth promoting effect in the experimental group when single substance prepared from manufacturing Examples 2, 5, 8, 10 (indirubin derivatives, Euodia daniellii extract, methyl vanillate, hesperidin, quercitrin alone), the composites prepared from Embodiments 2, 7, 9 respectively are treated on mouse nose hair follicles (vibrissa follicles).

Figure 5:
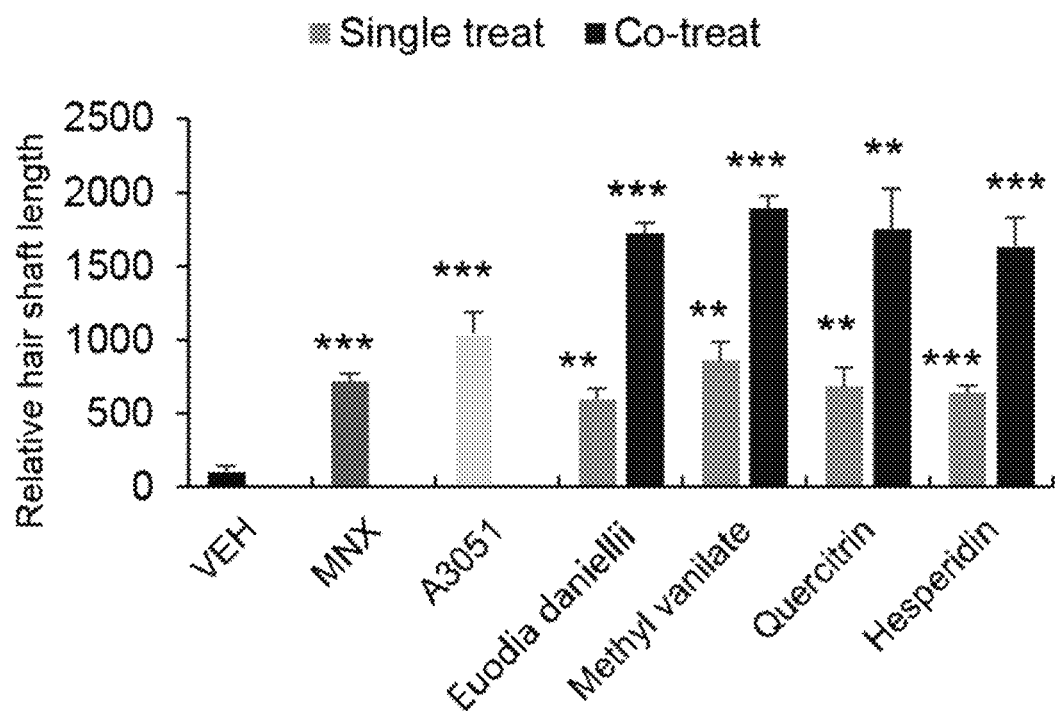
FIG. 5 is a graph showing the statistical analyses of changes of hair shaft growth length in each experimental group when treated with a composite prepared from manufacturing examples 2, 5, 8 to 10 (indirubin derivative, Euodia daniellii extract, methyl vanillate, hesperidin and quercitrin alone) or complexes prepared from embodiments 2 and 7 to 9 in mouse vibrissa follicles (data of the mean±SE, * $P<0.05$,  $P<0.005$, * $P<0.0005$ vs. control).

FIG. 5 is a graph showing the change in the length of hair shaft growth in the experimental group when single substance prepared from manufacturing Examples 2, 5, 8, 10 (indirubin derivatives, Euodia daniellii extract, methyl vanillate, hesperidin, quercitrin alone), the composites prepared from Embodiments 2, 7, 9, respectively, are treated on mouse nose hair follicles (vibrissa follicles). (data are expressed as mean, SD and * P<0.05,  P<0.005, * P<0.0005 vs. control).

As shown in FIGS. 4 and 5, it was confirmed that the composite of Euodia daniellii extract and indirubin derivatives significantly improved the hair fiber length of mouse nose hair follicles. Specifically, compared to the case of using the indirubin derivatives of the manufacturing examples 2, 5, 8, 10 and the extract alone (single treat), the case of using the composite of embodiments (co-treat) 7, 9 have 2 times higher effect. It was a significant increase of effect which was not expected when the indirubin derivatives were used alone or when the Euodia daniellii extract was used alone.

Therefore, it is found that the composite prepared from Embodiments 2, 7, 9 of the present invention can be used as a composition useful for preventing hair loss and promoting hair growth.

Experimental Example 5. Solubility Measurement for Active Ingredient of the Present Invention To determine emulsion solution, solubility of indirubin derivative, embodiment 2 is measured in the several oil and surfactants. After enough amount of indirubin derivative powder made from manufacturing example 2 is putted into each oil or surfactants (1 ml), it was into vortexing 30 min. The equilibrium state was reached by shaking for 72 hours at 37° C. with 50 rpm speed in an incubator, then centrifuged at 16,100×g for 5 min. The supernatant was diluted with methanol and analyzed by LC/MS/MS. The kind of above oil or surfactants and measured solubility are shown below table 1.

'Waters xevo TQ MS-ACQUITY UPLC System' is used as an analyses equipment. ACQUITY UPLC® BEH (C18, 1.7 μm, 2.1×50 mm) column was used for analyses at room temperature. Mobile phase is used after filtration of deionized distilled water including 0.1% formic acid and acetonitrile including 0.1% formic acid (30:70, v/v) with 0.2 μl membrane filter. The flow rate is 0.25 ml/min and it is analyzed by injection of 0.5 μl sample. There are LC/MS/MS conditions for Decursin analysis; Cone 38 V, Collison 32 V. Precursor ion and daughter ion are monitored 329 and 229 m/z, respectively.

TABLE 1

| Kind | Kind | Solubility (mg/ml) |
|---|---|---|
| Oil | Olive oil | 0.83 |
| | Sunflower oil | 1.35 |
| | Kolliphor EL | 5.4 |
| Surfactants | Tween 20 | 4.58 |
| | Tween 80 | 4.92 |
| Co-surfactant | Transcutor P | 1.15 |
| | Propylene glycol | 0.25 |
| | PEG 400 | 3.1 |

Figure 6:
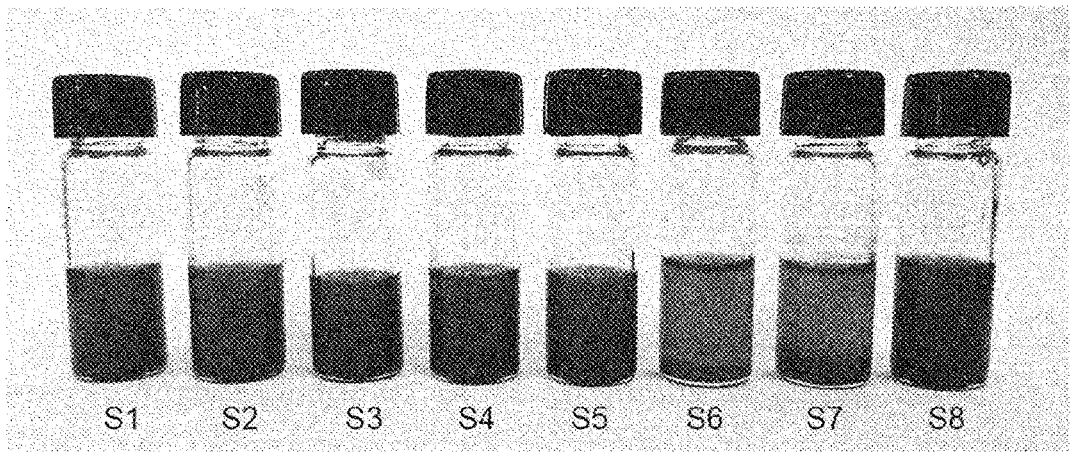
FIG. 6 is a photograph of an emulsion solution prepared by dissolving indirubin derivative (A3051) prepared from manufacturing Example 2 of the present invention in the various oils or surfactants, respectively.

FIG. 6 is photo of emulsion solution made by dissolving indirubin derivative made from Manufacturing example 2 of the present invention in oil or surfactant. As shown in FIG. 6 and Table 2, for the indirubin derivative made from manufacturing example 2 in according the present invention, composition forming emulsion solution which is established first by using Kolliphor® EL, Tween 20, Tween 80, PEG 400 show highest solubility among the emulsified solution. Above mentioned Kolliphor® EL, Tween 20 or Tween 80 and PEG 400 are harmless and safe. Therefore, these are stable and has been used for composition of various products used for human including application onto skin application.

Experimental Example 6. Ternary Diagram Analysis

Based on solubility experiment results, Kolliphor® EL is selected as emulsion and mixture of Tween 80 and PEG 400 are selected as a surfactants.

To confirm area of emulsion forming range, ternary phase diagram is completed by using H2O titration method the room temperature.

Surfactants mixtures are prepared by mixing surfactant Tween 80 and PEG 400 at each 1:1, 2:1 and 1:2 ratio. And, emulsion solution is made by mixing surfactant at a various ratio (0.5:9.5, 1:9. 2:8, 3:7, 4:6, 5:5, 6:4, 7:3, 8:2, 9:1, 9.5:0.5) with oil phase, Kolliphor® EL. While stirring above mentioned emulsion solution and loading water with a 1 ml/min rate of speed, area maintaining uniformly mixed state observed with naked eye is marked in the phase diagram and above ternary diagrams are presented FIGS. 7, 8 and 9.

Figure 7:
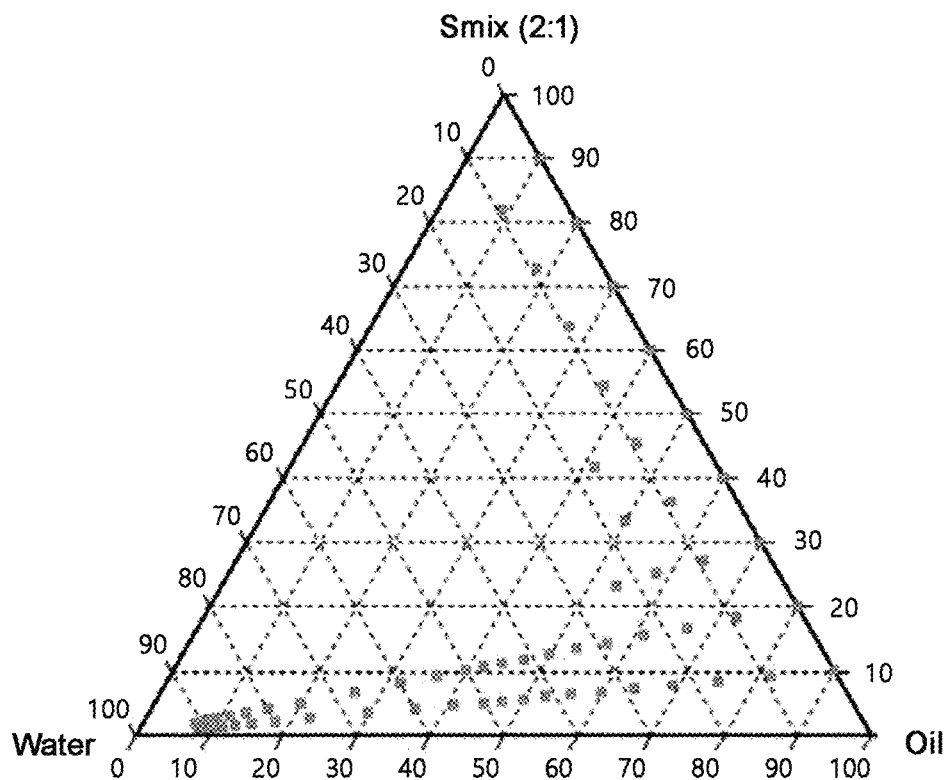
FIG. 7 is a ternary phase diagram for an emulsion solution prepared with a 2:1 ratio mixed surfactant of Tween 80 and PEG 400.
Figure 8:
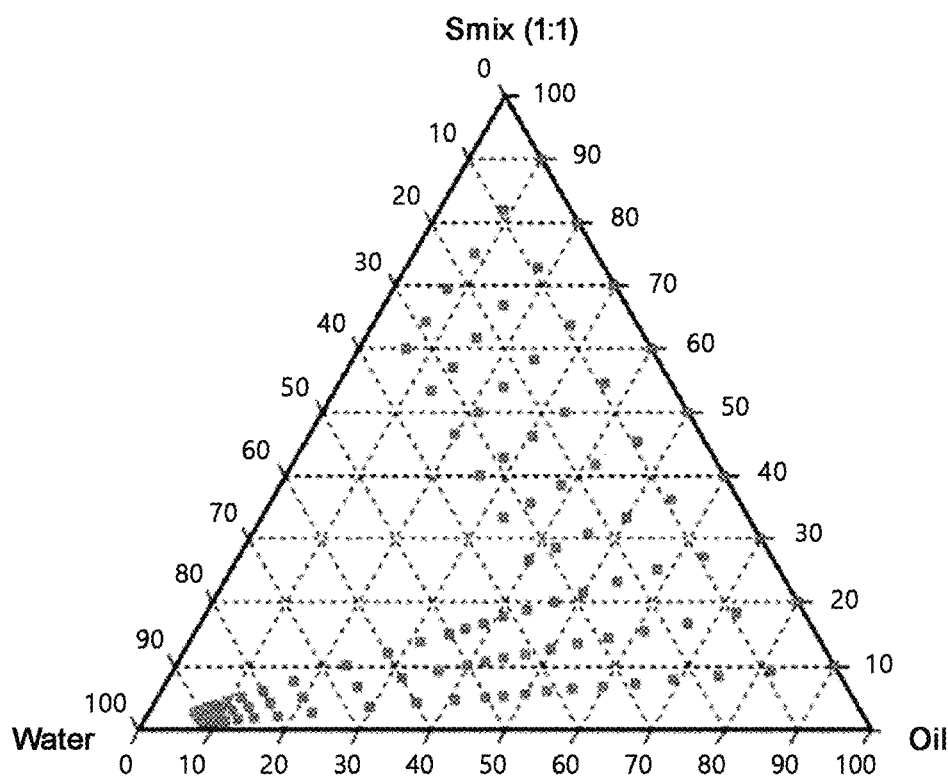
FIG. 8 is a ternary phase diagram for an emulsion solution prepared with a 1:1 mixed ratio of Tween 80 and PEG 400.
Figure 9:
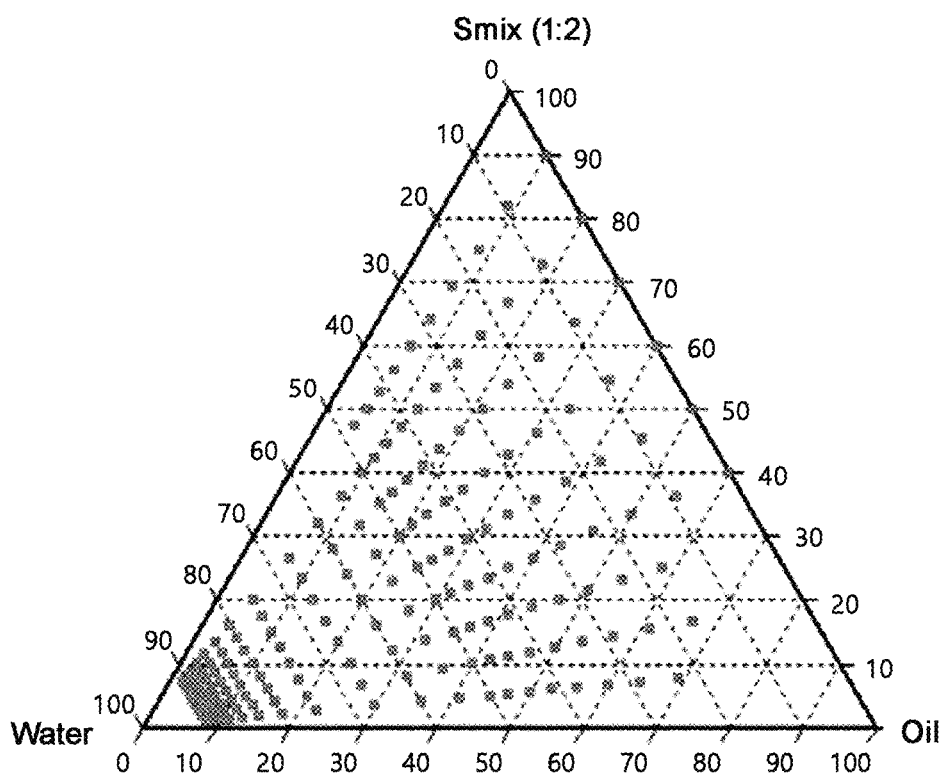
FIG. 9 is a ternary phase diagram for an emulsion solution prepared with a 1:2 ratio mixed surfactant of Tween 80 and PEG 400. In the ternary phase diagram of FIG. 9, the areas forming a stable emulsion are indicated by red dots.

FIG. 7 shows ternary diagram for emulsion solution made of surfactant mixed 2:1 ratio (Tween 80:PEG 400). FIG. 8 shows ternary diagram for emulsion solution made of surfactant mixed 1:1 ratio (Tween 80:PEG 400). FIG. 9 shows ternary diagram for emulsion solution made of surfactant mixed 1:2 ratio (Tween 80:PEG 400). In the ternary diagrams of FIGS. 7, 8 and 9, the areas forming stable emulsion are represented by red dots.

On the basis of the data presented in FIG. 7,8,9, emulsion solution using surfactants mixed Tween 80 and PEG 400 at a 1:2 ratio showed most wide range number, therefore, selected it is. After that, for final selection of ratio between above mentioned surfactants and emulsion, emulsion solution, droplet size, viscosity, zeta potential of emulsion solution produced with various ratio are compared.

Experimental Example 7. Formulation Development of a Composition for Preventing Hair Loss or Promoting Hair Growth To develop oil in water emulsion formulation for stable solubility and long-term stability of indirubin derivative made from manufacturing example 2, most stable emulsion solution is searched by mixing surfactants, polyethylene glycol and oil.

Emulsion solution is manufactured with surfactant, polyethylene glycol and oil selected in experimental example 6 in various ratios, 10:30:60 or 90:3:7. To manufacture emulsion including active ingredient on the present invention, emulsion was manufactured by adding active ingredient (indirubin derivative powder of manufacturing example 2) to make final 10% weight concentration for the total weight of entire composition and stirred overnight. (For example, if weight of total composition is 100 g, then indirubin derivative powder 20 g made from manufacturing example 2 was mixed with above mentioned emulsion solution, 80 g)

The solubilizer Cyclodextrin can be included in the above mentioned composition. Indirubin derivative (active ingredient) (100 part by weight) added with cyclodextrin (100 part by weight) is used in this experiment to increase solubilization of indirubin derivative.

Emulsion solution manufactured reveals as opaque red colored as seen by naked eyes. Above mentioned solubility, droplet size, viscosity, zeta potential for above mentioned emulsion solutions are analyzed and presented in Table 2.

TABLE 2

| Class | Emulsion solution (Kollipore ® EL:Tween 80:PEG400) 중량비 | Solubility (mg/ml) | Droplet size (nm) | Viscosity (mPas) | Zetapotential (mV) |
|---|---|---|---|---|---|
| F1 | 10:30:60 | 2.99 | 1525.7 | 23.33 | −5.14 |
| F2 | 20:26:54 | 3.58 | 921.3 | 44.46 | −6.87 |
| F3 | 30:23:47 | 3.81 | 624.9 | 59.12 | −7.23 |

TABLE 2-continued

| Class | Emulsion solution (Kollipore® EL:Tween 80:PEG400) 중량비 | Solubility (mg/ml) | Droplet size (nm) | Viscosity (mPas) | Zetapo-tential (mV) |
|---|---|---|---|---|---|
| F4 | 40:20:40 | 4.11 | 479.4 | 65.07 | −6.94 |
| F5 | 50:16:34 | 5.67 | 332.3 | 72.72 | −7.99 |
| F6 | 60:13:27 | 6.86 | 264.9 | 88.85 | −9.72 |
| F7 | 70:10:20 | 7.59 | 183.8 | 91.39 | −10.83 |
| F8 | 80:6:14 | 7.69 | 41.5 | 98.3 | −20.38 |
| F9 | 90:3:7 | 6.88 | 29.3 | 99.52 | −20.99 |

As shown on Table 2, droplet size decreased as oil contents increased and it is identified that all of them have appropriate physical properties to use for pharmaceutical or cosmetic compositions. But, F8 condition have most desirable size, viscosity, zeta-potential and solubility.

Experimental Example 8. Assessment for Safety Evaluation of the Formulation for the Emulsion Solution-1

To confirm stability of manufactured emulsion solution, F8, F10~12 emulsion solutions were made with a composition in below Table 3. Stability of above mentioned emulsion solutions are measured based on relative solubility (%) change at the low temperature (4° C.) and room temperature (25° C.). Relative solubility (%) are recorded up to 3 months and presented in FIG. 10 and FIG. 11.

TABLE 3

| Class | Emulsion solution | | | Active Ingredient | Solubilizer (2- | |
|---|---|---|---|---|---|---|
| | Oil | surfactants | Polyethylene glycol | Indirubin derivative of embodiment 2 | hydroxy β-cyclodextrin) | Aqua state |
| DMSO Control | — | — | — | 12.5 g | 12.5 g | Distilled water 100 g |
| F8 | Kollipore® EL 80 g | Tween 80 6.7 g | PEG400 13.3 g | 12.5 g | 12.5 g | Distilled water 100 g |
| F10 | — | — | PEG400 100 g | 12.5 g | 12.5 g | Distilled water 100 g |
| F11 | — | Tween 80 100 g | — | 12.5 g | 12.5 g | Distilled water 100 g |
| F12 | Kollipore® EL 100 g | — | — | 12.5 g | 12.5 g | Distilled water 100 g |

Figure 10:
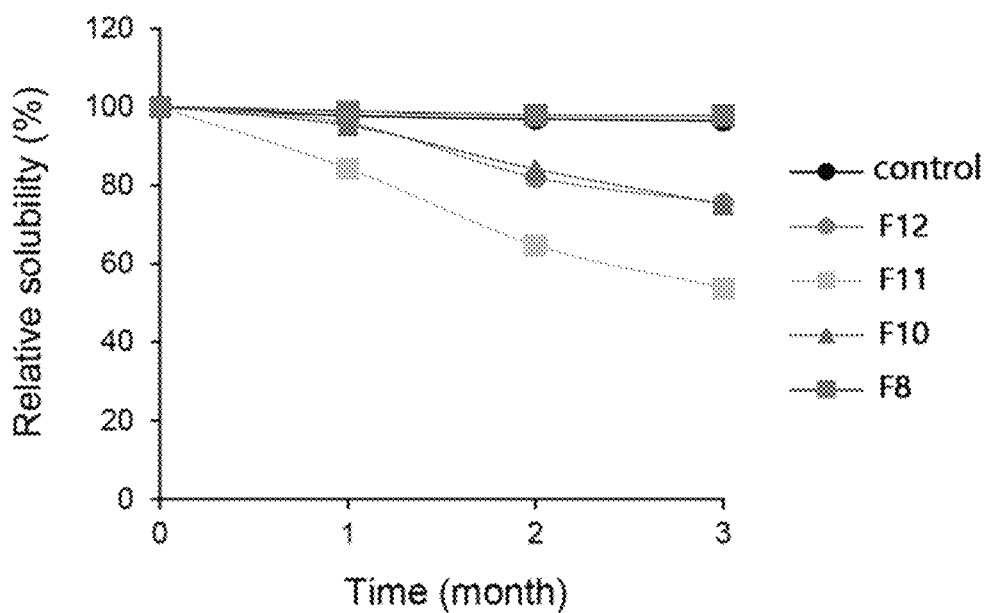
FIG. 10 is a graph showing the relative changes in solubility % of the F8, F10-12 emulsion formulations at room temperature (25° C.).
Figure 11:
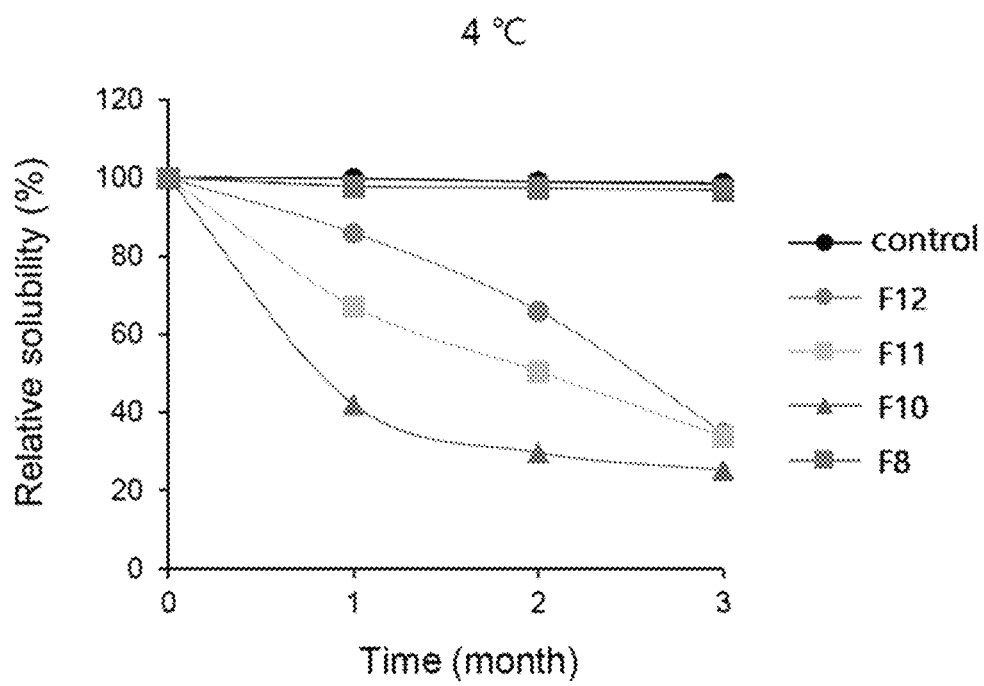
FIG. 11 is a graph showing the relative change in solubility % of F8, F10-12 emulsion formulations at low temperature (4° C.).

FIG. 10 represents graphs showing relative solubility (%) change of F8, F10~12 emulsion solutions at room temperature (25° C.). FIG. 22 is graph showing relative solubility (%) change of F8, F10~12 emulsion solution at a low temperature (4° C.).

As shown in the FIG. 10, 11 and Table 3, after leaving 3 months at the low temperature and room temperature, relative solubility changes were observed. It is identified that solubility (%) change difference was little between right after manufacturing and after 3 months in case of emulsion solution (F8). Whereas, there was over 40% solubility change between right after manufacturing and 3 months after at the low temperature and room temperature in case of emulsion (F12, 11, 10) which is made from solution composition different with the present invention. Specifically, solubility dropped rapidly over 80% at the low temperature condition.

Experimental Example 9. Assessment of Dependent Stability of Emulsion Solution-2

F8, F10-F12 emulsion formulations were manufactured with composition of above mentioned Table 3 to confirm whether activity of active ingredient of indirubin derivative, manufacturing example 2 is remained stable in the emulsion formulation. Activation stability of indirubin derivative in the above mentioned emulsion formulation is measured based on relative Wnt reporter activity (%) change at the low temperature (4° C.) and room temperature (25° C.). Relative Wnt reporter activity (%) right from manufacturing until 3 months are recoded on FIG. 12 and FIG. 13.

Above mentioned Wnt reporter activity (%) is measured through the following ways. The Wnt reporter activity (%) is measured 24 hours after treatment HEK-pTOPFLASH reporter cells with active ingredient made with emulsion formulation.

Figure 12:
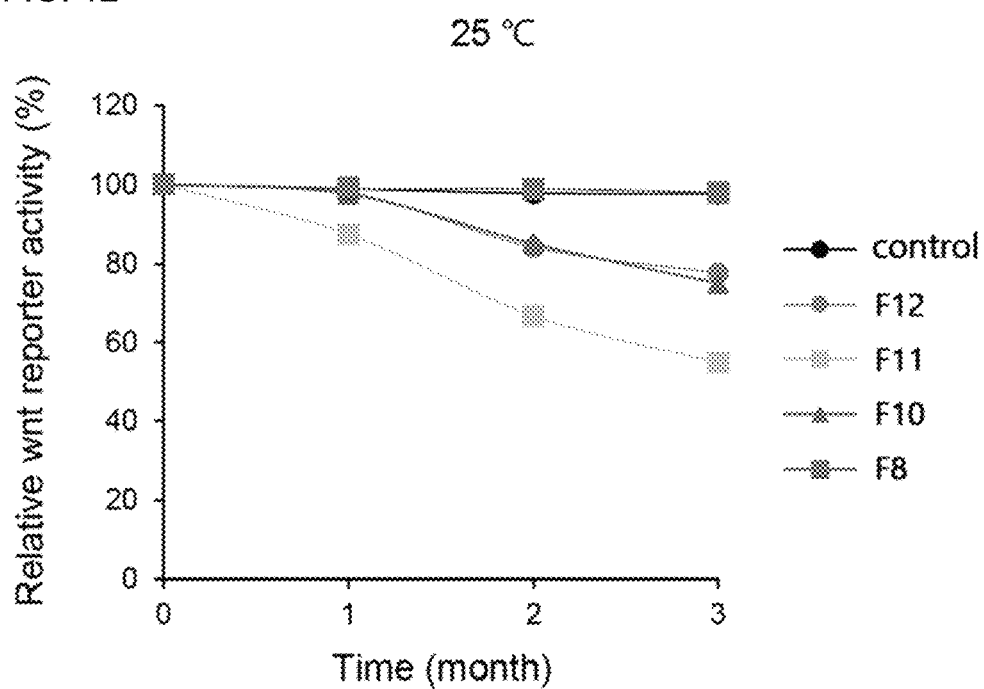
FIG. 12 is a graph showing the relative change in Wnt reporter activity % of F8, F10-12 emulsion formulations at room temperature (25° C.).
Figure 13:
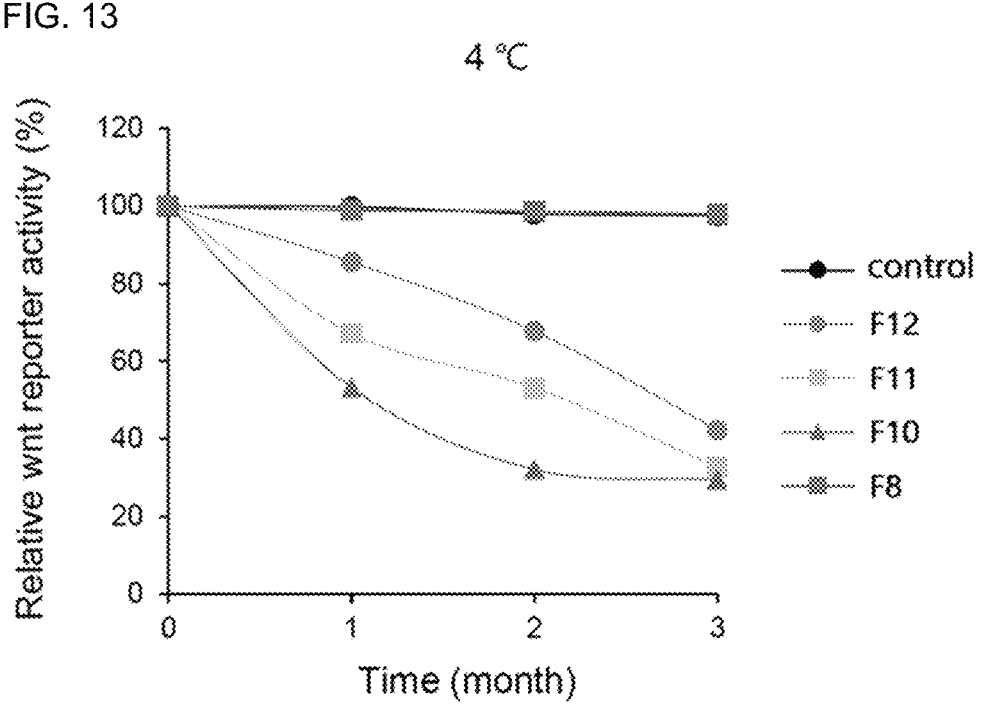
FIG. 13 is a graph showing the relative change in Wnt reporter activity % of F8, F10-12 emulsion formulations at low temperature (4° C.).

The graphs in FIG. 12 show relative Wnt/beta-catenin signaling reporter activity (%) change of F8, F10-F12 emulsion solutions measured at a room temperature (25° C.). FIG. 13 is graph showing relative Wnt/beta-catenin signaling reporter (%) change of F8, F10-F12 emulsion solution at a low temperature (4° C.).

As shown in FIG. 12 and FIG. 13, relative Wnt reporter activity (%) change were observed after leaving emulsion solution for 3 months at the low temperature and room temperature. It is identified that Wnt reporter activity (%) change difference was little between right after manufacturing and after 3 months in case of emulsion solution (F8). Whereas, the Wnt reporter activity (%) was decrease over 40% after 3 months at the low temperature and room temperature in case of emulsion (F12, 11, 10) which is made from solution composition different with the present invention. Specifically, it is identified that Wnt reporter activity (%) dropped rapidly over 80% at the low temperature condition.

Formulation Example 1: Cream Cosmetic Composition for Preventing Hair Loss or Promoting Hair Growth In this formulation example, a cream-type cosmetic composition for preventing hair loss or promoting hair growth containing a complex of the Euodia daniellii extract and the indirubin derivative of Formula 1 as an active ingredient is prepared. Ingredients including the composite of embodiment 1 were mixed according to the following content to prepare a creamy cosmetic composition for preventing hair loss or promoting hair growth.

4.0 wt % of the composite of Embodiment 1
2.0 wt % of the Glycerin.
0.2 wt % of the Paraben
2.0 wt % of the allantoin
3.0 wt % of the betaine 1.0 wt % of the Sodium Hyaluronate.
5.0 wt % of the tocopherol acetate
2.0 wt % of the Shea Butter
1.0 wt % of the trehalose
Weight percent % of preservative and fragrance.
Purified water to 100% by weight
Total 100% by weight Formulation Example 2: Pharmaceutical Composition for Preventing Hair Loss or Promoting Hair Growth (Ointment)

In this formulation example, a pharmaceutical composition (ointment) for preventing hair loss or promoting hair growth containing a complex of the Euodia daniellii extract and the indirubin derivative of Formula 1 as an active ingredient is prepared.
Ingredients including the composite of embodiment 1 were mixed according to the following content to prepare a pharmaceutical composition (ointment) for wound healing.
10.0 wt % of the composite of Embodiment 1
8.0 wt % of the diethyl sebacate.
5.0 wt % of the hard solder.
6.0 wt % of the Polyoxyethylene oleyl ether phosphate
Weight percent % of quantity of sodium benzoate
Vaseline to 100% by weight
Total 100% by weight Formulation Example 3 Preparation of Hair Tonic 10.0 wt % of the composite of Embodiment 1
0.1 wt % of the resorcinol.
0.05 wt % of the menthol
0.2 wt % of the panthenol
0.1 wt % of the salicylic acid
0.1 wt % of the tocopheryl acetate
0.1 wt % of the Pyridoxine HCl
5.0 wt % of the castor oil
suitable amount of pigment
suitable amount of perfume
suitable amount of ethanol
remaining amount of purified water
Total 100% by weight Formulation Example 4 Preparation of Hair Conditioner 2.5 wt % of the composite of Embodiment 1
3.5 wt % of the cetanol
1.5% of the Self-emulsifying glycerin monostearate
2.5% of the Propylene glycol
7.0% of the Stearylmethylbenzyl Ammonium Chloride (25%)
0.3% of the Methyl p-Hydroxybenzoate
suitable amount of pigment
suitable amount of perfume
remaining amount of purified water
Total 100% by weight Formulation Example 5. Preparation of Hair Lotion 5.0 wt % of the composite of Embodiment 1
2.0% of the resorcinol
2.0% of the menthol
0.5% of the panthenol
0.1% of the Piroctone Olamine
0.5% of the perfume, pigment
remaining amount of purified water
Total 100% by weight Formulation Example 6. Preparation of Hair Soap 0.1 wt % of the composite of Embodiment 1
0.2% of the titanium dioxide
0.8% of the polyethylene glycol
0.5% of the Glycerin
0.05% of the ethylenediamine tetra acetic acid
1.0% of the Sodium
suitable amount of pigment
suitable amount of soap perfume
remaining amount of cosmetic soap base (13% moisture, parts by weight)
Total 100% by weight Formulation Example 7. Application to Milk 99.9 wt % of the milk
0.1 wt % of the composite of Embodiment 1

Formulation Example 8. Manufacturing of Beverages 10 mg of the composite of Embodiment 1
50 mg of the Calcium Lactate
5 mg of the citric acid
10 mg of the nicotinamide
3 mg of the Riboflavin Sodium Hydrochloride
2 mg of the Pyridoxine HCl
10 mg of the arginine
10 mg of the sucrose fatty acid ester
200 ml of water

The invention claimed is:
1. A method for treating or reducing hair loss, promoting hair generation, or hair growth comprising administering to subject a composition comprising indirubin derivatives as an active ingredient,
wherein the indirubin derivatives are one or more selected from the group consisting of Formula 1 to Formula 4

[Formula 1]

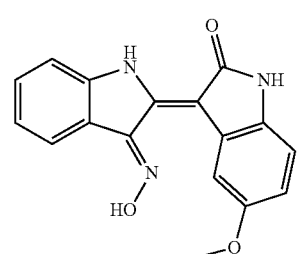

[Formula 2]

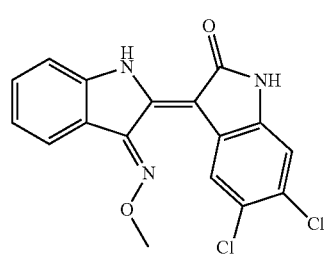

-continued

[Formula 3]

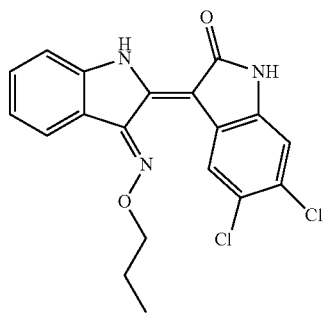

[Formula 4]

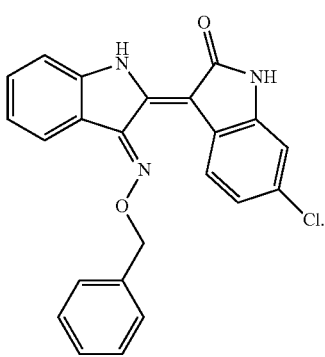

2. The method for treating or reducing hair loss, promoting hair generation, or hair growth according to claim 1, wherein the composition further comprises one or more selected from the group consisting of Euodia daniellii extract, Persicaria hydropiper extract, Hovenia dulcis extract, methyl vanillate, hesperidin and quercitrin.

3. The method for treating or reducing hair loss, promoting hair generation, or hair growth according to claim 2, wherein the extracts are extracted from the stem, leaves, or their pulverized products thereof and mixtures thereof with a solvent selected from the group consisting of water, alcohols having 1 to 4 carbon atoms, DMSO, n-hexane, ethyl acetate and mixed solvents thereof.

4. The method for treating or reducing hair loss, promoting hair generation, or hair growth according to claim 2, wherein the indirubin derivative and the extract are mixed, the indirubin derivative is included in an amount of 5 to 15 parts by weight based on the dry weight part 10 of the extract, and wherein the indirubin derivative and one or more small molecular compound selected from methyl vanillate, hesperidin and quercitrin are mixed, the indirubin derivative is mixed at a ratio of 1 to 20 moles based on 1 mole of the small molecular compound.

5. The method for treating or reducing hair loss, promoting hair generation, or hair growth according to claim 2, wherein the composition is emulsion formulation further comprising oil, surfactant and polyethylenglycol, and wherein mixture ratio of the oil:the surfactants:the polyethylene glycol is 0.3-30:1:2-2.5.

* * * * *